(12) United States Patent
Walter et al.

(10) Patent No.: US 7,332,518 B2
(45) Date of Patent: Feb. 19, 2008

(54) CARBOXAMIDES AS FUNGICIDES IN AGRICULTURE

(75) Inventors: Harald Walter, Basel (CH); Stephan Trah, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 345 days.

(21) Appl. No.: 10/470,069

(22) PCT Filed: Jan. 24, 2002

(86) PCT No.: PCT/EP02/00717

§ 371 (c)(1),
(2), (4) Date: Jan. 12, 2004

(87) PCT Pub. No.: WO02/059086

PCT Pub. Date: Aug. 1, 2002

(65) Prior Publication Data

US 2004/0138265 A1    Jul. 15, 2004

(30) Foreign Application Priority Data

Jan. 25, 2001  (GB) .................................. 0101996.7

(51) Int. Cl.
*A61K 31/415* (2006.01)
*A61K 31/38* (2006.01)
*C07D 231/10* (2006.01)
*C07D 333/22* (2006.01)
*C07D 307/34* (2006.01)

(52) U.S. Cl. ...................... 514/406; 514/438; 514/448; 514/461; 548/364.1; 548/373.1; 549/72; 549/73; 549/467

(58) Field of Classification Search ............. 548/364.4, 548/373.1; 514/406

See application file for complete search history.

(56) References Cited

U.S. PATENT DOCUMENTS

| 5,004,816 A |   | 4/1991  | Mori et al. |         |
|-------------|---|---------|-------------|---------|
| 5,438,070 A |   | 8/1995  | Eicken et al. |       |
| 5,480,897 A |   | 1/1996  | Eicken et al. |       |
| 5,756,524 A | * | 5/1998  | Riordan et al. | 514/346 |
| 5,998,450 A |   | 12/1999 | Eicken et al. |       |

FOREIGN PATENT DOCUMENTS

| EP | 0 315 502    | 5/1989  |
|----|--------------|---------|
| EP | 0737682      | 10/1996 |
| EP | 0824099      | 2/1998  |
| EP | 1 036 793    | 9/2000  |
| WO | 95 25723     | 9/1995  |
| WO | 00 09482     | 2/2000  |
| WO | WO 01/49664 A1 | 7/2001 |

* cited by examiner

*Primary Examiner*—Johann Richter
*Assistant Examiner*—Ebenezer Sackey
(74) *Attorney, Agent, or Firm*—Rebecca Howard

(57) ABSTRACT

The invention concerns novel carboxamides of formula (I) wherein A is (A1), (A2), (A3), (A4), (A5); Q is (Q1), (Q2), (Q3), (Q4), (Q5), (Q6); $R_1$ is $CH_2 R_2$, $CH_2CH=CHR_2$, $CH=C=CHR_2$ or $COR_3$; $R_2$ is hydrogen, $C_1$-$C_6$alkyl, $C_1$-$C_6$haloalkyl, $C_2$-$C_6$alkenyl, $C_2$-$C_6$alkynyl, $C_3$-$C_7$cycloalkyl, $COOC_1$-$C_4$alkyl, $COOC_3$-$C_6$alkenyl, $COOC_3$-$C_6$alkynyl or CN; $R_3$ is $C_1$-$C_6$alkyl, $C_1$-$C_6$alkyl substituted by halogen, $C_1$-$C_6$alkoxy or $C_1$-$C_6$haloalkoxy; or is $C_1$-$C_6$alkylthio, $C_1$-$C_6$haloalkylthio, $C_1$-$C_6$alkoxy, $C_1$-$C_6$haloalkoxy; $C_3$-$C_6$alkenyloxy or $C_3$-$C_6$haloalkenyloxy; $C_3$-$C_6$haloalkenyloxy; $C_3$-$C_6$alkynyloxy or $C_3$-$C_6$haloalkynyloxy; $R_4$ is methyl, $CF_2Cl$, $CF_3$, $CF_2H$, $CFH_2$, Cl or Br, $R_5$ is methyl, $CF_3$, $CH_2OCH_3$ or $CH_2OCF_3$; $R_6$ is hydrogen, fluoro, $CF_3$ or methyl; $R_7$ is hydrogen, methyl or halogen; and Z is phenyl, halophenyl, $C_5$-$C_7$cycloalkyl, $C_5$-$C_7$cycloalkyl substituted by $C_1$-$C_3$alkyl, $C_1C_3$haloalkyl or halogen, or a group of the form —$CHR_8$—$CH_2$—$CHR_9R_{10}$ wherein $R_8$, $R_9$ and $R_{10}$ are independently of each other $C_1$-$C_3$alkyl. The novel compounds have plant-protective properties and are suitable for protecting plants against infestation by phytopathogenic microorganisms, in particular fungi.

11 Claims, No Drawings

CARBOXAMIDES AS FUNGICIDES IN AGRICULTURE

This application is a 371 of International Application No. PCT/EP02/00717 filed Jan. 24, 2002, which claims priority to GB 0101996.7, filed Jan. 25, 2001.

The present invention relates to novel carboxamides which have microbicidal activity, in particular fungicidal activity. The invention also relates to the preparation of these substances, to agrochemical compositions which comprise at least one of the novel compounds as active ingredient, to the preparation of the compositions mentioned, to a method of protecting plants against attack or infestation by phytopathogenic organisms, preferably fungi, by applying the novel compounds as specified hereinafter to a part and/or the site of a plant and to the use of said novel compounds or compositions thereof in agriculture and horticulture for controlling or preventing infestation of plants by phytopathogenic microorganisms, preferably fungi.

The carboxamides of the present invention have the general formula I

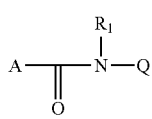

(I)

wherein

A is

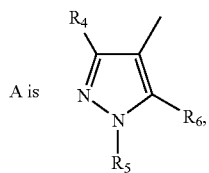 (A1)

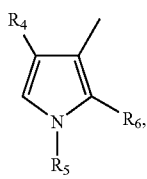 (A2)

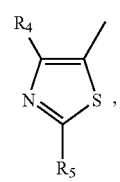 (A3)

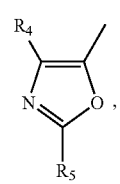 (A4)

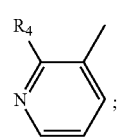 (A5)

Q is

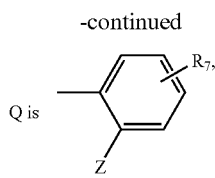 (Q1)

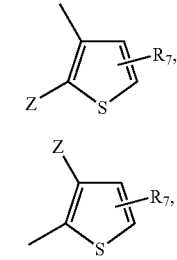 (Q2)

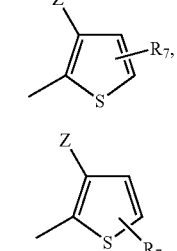 (Q3)

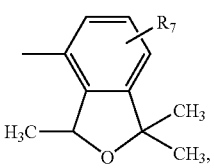 (Q4)

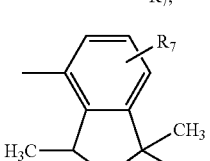 (Q5)

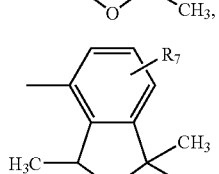 (Q6)

$R_1$, is $$CH_2\!-\!\!\!=\!\!\!-R_2,$$

$CH_2CH=CHR_2$, $CH=C=CHR_2$ or $COR_3$;

$R_2$ is hydrogen, $C_1$-$C_6$alkyl, $C_1$-$C_6$haloalkyl, $C_2$-$C_6$alkenyl, $C_2$-$C_6$alkynyl, $C_3$-$C_7$cycloalkyl, $COOC_1$-$C_4$alkyl, $COOC_3$-$C_6$alkenyl, $COOC_3$-$C_6$alkynyl or CN;

$R_3$ is $C_1$-$C_6$alkyl, $C_1$-$C_6$alkyl substituted by halogen, $C_1$-$C_6$alkoxy or $C_1$-$C_6$haloalkoxy; or is $C_1$-$C_6$alkylthio, $C_1$-$C_6$haloalkylthio, $C_1$-$C_6$alkoxy, $C_1$-$C_6$haloalkoxy; $C_3$-$C_6$alkenyloxy or $C_3$-$C_6$haloalkenyloxy; $C_3$-$C_6$alkynyloxy or $C_3$-$C_6$haloalkynyloxy;

$R_4$ is methyl, $CF_2Cl$, $CF_3$, $CF_2H$, $CFH_2$, Cl or Br;

$R_5$ is methyl, $CF_3$, $CH_2OCH_3$ or $CH_2OCF_3$;

$R_6$ is hydrogen, fluoro, $CF_3$ or methyl;

$R_7$ is hydrogen, methyl or halogen, and

Z is phenyl, halophenyl, $C_5$-$C_7$cycloalkyl, $C_5$-$C_7$cycloalkyl substituted by $C_1$-$C_3$alkyl, $C_1$-$C_3$haloalkyl or halogen, or a group of the form

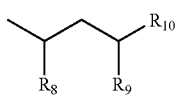

wherein $R_8$, $R_9$ and $R_{10}$ are independently of each other $C_1$-$C_3$alkyl.

Surprisingly, it has now been found that the compounds of formula I exhibit improved biological properties which render them more suitable for the practical use in agriculture and horticulture.

Where asymmetrical carbon atoms are present in the compounds of formula I, these compounds are in optically active form. The invention relates to the pure isomers, such as enantiomers and diastereomers, as well as to all possible mixtures of isomers, e.g. mixtures of diastereomers, racemates or mixture of racemates.

Within the present specification alkyl denotes methyl, ethyl, n-propyl, n-butyl, n-pentyl, n-hexyl, isopropyl, isobutyl, sec.-butyl, tert.-butyl, isopentyl, neopentyl and isohexyl. Non-branched alkyl is preferred. Alkyl as part of other radicals such as alkoxy, haloalkyl, etc. is understood in an analogous way. Halogen will be understood generally as meaning fluoro, chloro, bromo or iodo. Fluoro, chloro or bromo are preferred meanings. Halogen as part of other radicals such as haloalkyl, haloalkoxy, etc. is understood in an analogous way.

Haloalkyl is preferably $C_1$-$C_6$alkyl, more preferably lower alkyl, that is linear or branched and is substituted by one or more, for example in the case of halo-ethyl up to five, halogen atoms, especially fluorine. As example is trifluoromethyl.

Haloalkoxy is preferably $C_1$-$C_6$alkoxy, that is linear or branched and that is substituted by one or more halogen atoms, especially fluorine; trifluoromethoxy, perfluoroethyl and 1,1,2,2-tetrafluoroethoxy are preferred.

Cycloalkyl is, depending on the ring size, cyclopropyl, cyclobutyl, cyclopentyl, cyclohexyl or cycloheptyl.

Alkenyl will be understood as meaning straight-chain or branched alkenyl such as allyl, methallyl, 1-methylvinyl or but-2-en-1-yl. Preferred alkenyl radicals contain 3 to 4 carbon atoms in the chain, i.e. allyl or 2-butenyl. This also applies where alkenyl is part of haloalkenyl, alkenyloxy or haloalkenyloxy.

Alkynyl can likewise, in accordance with the number of carbon atoms, be straight-chain or branched and is typically propargyl, but-2-yn-1-yl or but-1-yn-3-yl. The same definitions apply where alkynyl is part of alkynyloxy or haloalkynyloxy.

Among the compounds of formula I according to the present invention the following groups of compounds are preferred. These groups are those wherein
A is A1, A2, A3, A4 or A5, or
A is A1, A2 or A3, or
A is A1 or A2, or
Q is Q1, Q2, Q3, Q4, Q5 or Q6, or
Q is Q5 or Q6, or
Q is Q1 or Q6, or
$R_1$ is

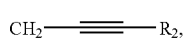

$CH_2CH=CHR_2$, $CH=C=CHR_2$ or $COR_3$, or
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl, or
$R_2$ is hydrogen ; or
$R_3$ is $C_1$-$C_6$alkyl, $C_1$-$C_6$alkyl substituted by fluoro, chloro, bromo, $C_1$-$C_4$alkoxy or $C_1$-$C_4$haloalkoxy; or is $C_1$-$C_4$alkoxy, $C_1$-$C_4$haloalkoxy; $C_3$-$C_4$alkenyloxy or $C_3$-$C_6$alkynyloxy; or
$R_3$ is $C_1$-$C_4$alkyl, $C_1$-$C_4$alkoxy-$C_1$-$C_4$alkyl or $C_1$-$C_4$alkoxy; or
$R_3$ is $C_1$-$C_3$alkyl, $C_1$-$C_3$alkoxy-methyl or $C_1$-$C_3$alkoxy; or
$R_4$ is methyl, $CF_2Cl$, $CF_3$, $CF_2H$, $CFH_2$, Cl or Br, or
$R_5$ is methyl, $CF_3$, $CH_2OCH_3$ or $CH_2OCF_3$, or
$R_6$ is hydrogen, fluoro, $CF_3$ or methyl, or
$R_7$ is hydrogen, methyl or halogen, or
Z is phenyl, halophenyl, $C_5$-$C_7$cycloalkyl unsubstituted or substituted by $C_1$-$C_3$alkyl, $C_1$-$C_3$haloalkyl or halogen, or a group of the form

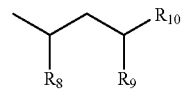

wherein $R_8$, $R_9$ and $R_{10}$ are independently of each other $C_1$-$C_3$alkyl, or
Z is phenyl, halophenyl or $C_5$-$C_7$cycloalkyl unsubstituted or substituted by $C_1$-$C_3$alkyl, $C_1$-$C_3$haloalkyl or halogen, or
Z is a group of the form

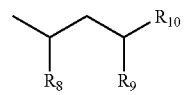

wherein $R_8$, $R_9$ and $R_{10}$ are independently of each other $C_1$-$C_3$alkyl.

Within the group of compounds of formula I, those compounds are preferred wherein
A is A1, A2, A3, A4 or A5;
Q is Q1, Q2, Q3, Q4, Q5 or Q6;
$R_1$ is

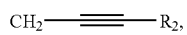

$CH_2CH=CHR_2$, $CH=C=CHR_2$ or $COR_3$;
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;
$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy;
$R_4$ is methyl, $CF_2Cl$, $CF_3$, $CF_2H$, $CFH_2$, Cl or Br;
$R_5$ is methyl, $CF_3$, $CH_2OCH_3$ or $CH_2OCF_3$;
$R_6$ is hydrogen, fluoro, $CF_3$ or methyl;
$R_7$ is hydrogen, methyl or halogen; and
Z is phenyl, halophenyl, $C_5$-$C_7$cycloalkyl unsubstituted or substituted by $C_1$-$C_3$alkyl, $C_1C_3$haloalkyl or halogen, or a group of the form

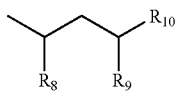

wherein $R_8$, $R_9$ and $R_{10}$ are independently of each other $C_1$-$C_3$alkyl (subgroup B1).

Within the subgroup B1 of compounds of formula I those compounds are preferred wherein
A is A1, A2, A3, A4 or A5;
Q is Q1;
$R_1$ is

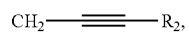

$CH_2CH=CHR_2$, $CH=C=CHR_2$ or $COR_3$;
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;
$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy;
$R_4$ is methyl, $CF_2Cl$, $CF_3$, $CF_2H$, $CFH_2$, Cl or Br;
$R_5$ is methyl, $CF_3$, $CH_2OCH_3$ or $CH_2OCF_3$;
$R_6$ is hydrogen, fluoro, $CF_3$ or methyl;
$R_7$ is hydrogen, methyl or halogen; and
Z is phenyl, halophenyl, $C_5$-$C_7$cycloalkyl unsubstituted or substituted by $C_1$-$C_3$alkyl, $C_1$-$C_3$haloalkyl or halogen, or a group of the form

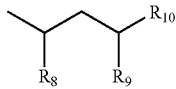

wherein $R_8$, $R_9$ and $R_{10}$ are independently of each other $C_1$-$C_3$alkyl (subgroup B2).

Within the subgroup B2 are those compounds more preferred wherein
A is A1, A2, A3, A4 or A5;
Q is Q1;
$R_1$ is

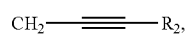

$CH_2CH=CHR_2$, $CH=C=CHR_2$ or $COR_3$;
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;
$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy;
$R_4$ is methyl, $CF_2Cl$, $CF_3$, $CF_2H$, $CFH_2$, Cl or Br;
$R_5$ is methyl, $CF_3$, $CH_2OCH_3$ or $CH_2OCF_3$;
$R_6$ is hydrogen, fluoro, $CF_3$ or methyl;
$R_7$ is hydrogen, methyl or halogen; and
Z is phenyl, halophenyl or a group of the form

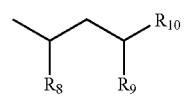

wherein $R_8$, $R_9$ and $R_{10}$ are independently of each other $C_1$-$C_3$alkyl (subgroup B21).

Within the subgroup B2 are those compounds preferred wherein.
A is A1, A2, A3, A4 or A5;
Q is Q1;
$R_1$ is

$CH_2CH=CHR_2$, $CH=C=CHR_2$ or $COR_3$;
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;
$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy;
$R_4$ is methyl, $CF_2Cl$, $CF_3$, $CF_2H$, $CFH_2$, Cl or Br;
$R_5$ is methyl, $CF_3$, $CH_2OCH_3$ or $CH_2OCF_3$;
$R_6$ is hydrogen, fluoro, $CF_3$ or methyl;
$R_7$ is hydrogen, methyl or halogen; and
Z is $C_5$-$C_7$cycloalkyl unsubstituted or substituted by $C_1$-$C_3$alkyl, $C_1$-$C_3$haloalkyl or halogen (subgroup B22).

Another group of compounds of formula I within the subgroup B1 are those wherein
A is A1 or A2;
Q is Q5 or Q6
$R_1$ is

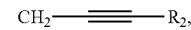

$CH_2CH=CHR_2$, $CH=C=CHR_2$ or $COR_3$;
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;
$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy;
$R_4$ is methyl, $CF_2Cl$, $CF_3$, $CF_2H$, $CFH_2$, Cl or Br;
$R_5$ is methyl, $CF_3$, $CH_2OCH_3$ or $CH_2OCF_3$;
$R_6$ is hydrogen, fluoro, $CF_3$ or methyl; and
$R_7$ is hydrogen, methyl or halogen (subgroup B3).

Within the subgroup B1 are those compounds of formula I preferred wherein
A is A1 or A2;
Q is Q2, Q3 or Q4;

$R_1$ is

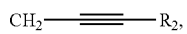

$CH_2CH=CHR_2$, $CH=C=CHR_2$ or $COR_3$;
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;
$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy;
$R_4$ is methyl, $CF_2Cl$, $CF_3$, $CF_2H$, $CFH_2$, Cl or Br;
$R_5$ is methyl, $CF_3$, $CH_2OCH_3$ or $CH_2OCF_3$;
$R_6$ is hydrogen, fluoro, $CF_3$ or methyl;
$R_7$ is hydrogen, methyl or halogen; and
Z is phenyl, halophenyl, $C_5$-$C_7$cycloalkyl unsubstituted or substituted by $C_1$-$C_3$alkyl, $C_1$-$C_3$haloalkyl or halogen, or a group of the form

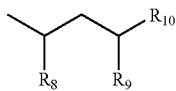

wherein $R_8$, $R_9$ and $R_{10}$ are independently of each other $C_1$-$C_3$alkyl (subgroup B13).

From subgroup B1 are further preferred compounds of formula I wherein
A is A1, A2 or A3;
Q is Q1 or Q6;
$R_1$ is

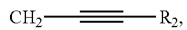

$CH_2CH=CHR_2$, $CH=C=CHR_2$ or $COR_3$;
$R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;
$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy;
$R_4$ is methyl, $CF_2Cl$, $CF_3$, $CF_2H$, $CFH_2$, Cl or Br;
$R_5$ is methyl, $CF_3$, $CH_2OCH_3$ or $CH_2OCF_3$;
$R_6$ is hydrogen, fluoro, $CF_3$ or methyl;
$R_7$ is hydrogen, methyl or halogen; and
Z is phenyl, halophenyl or $C_5$-$C_7$cycloalkyl unsubstituted or substituted by $C_1$-$C_3$alkyl, $C_1$-$C_3$haloalkyl or halogen (subgroup B4).

In the above listed subgroups further preference is given to those wherein
$R_2$ is hydrogen; or
$R_3$ is $C_1$-$C_4$alkyl, $C_1$-$C_4$alkoxy-$C_1$-$C_4$alkyl or $C_1$-$C_4$alkoxy; or
$R_3$ is $C_1$-$C_3$alkyl, $C_1$-$C_3$alkoxy-methyl or $C_1$-$C_3$alkoxy; or a group wherein
$R_2$ is hydrogen; and $R_3$ is $C_1$-$C_3$alkyl, $C_1$-$C_3$alkoxy-methyl or $C_1$-$C_3$alkoxy.

Preferred individual compounds of the formula I are:
1-methyl-4-trifluoromethyl-1H-pyrrole-3-carboxylic acid (2-methoxyacetyl)-[2'(4-fluorophenyl)phenyl]amide,
1-methyl-4-trifluoromethyl-1H-pyrrole-3-carboxylic acid (2-methoxyacetyl)-[2'(4-chlorophenyl)phenyl]amide,
1-methyl-4-trifluoromethyl-1H-pyrrole-3-carboxylic acid (2-propargyl)-[2'(4-fluorophenyl)phenyl]amide,
1-methyl-4-trifluoromethyl-1H-pyrrole-3-carboxylic acid (2-propargyl)-[2'(4-chlorophenyl)phenyl]amide,
1-methyl-4-trifluoromethyl-1H-pyrrole-3-carboxylic acid (2-acetyl)-[2'(4-fluorophenyl)phenyl]amide,
1-methyl-4-trifluoromethyl-1H-pyrrole-3-carboxylic acid (2-acetyl)-[2'(4-chlorophenyl)phenyl]amide,
1-methoxymethyl-4-trifluoromethyl-1H-pyrrole-3-carboxylic acid (2-methoxyacetyl)-[2'(4-fluorophenyl)phenyl]amide,
1-methoxymethyl-4-trifluoromethyl-1H-pyrrole-3-carboxylic acid (2-methoxyacetyl)-[2'(4-chlorophenyl)phenyl]amide,
1-methoxymethyl-4-trifluoromethyl-1H-pyrrole-3-carboxylic acid (2-propargyl)-[2'(4-fluorophenyl)phenyl]amide,
1-methoxymethyl-4-trifluoromethyl-1H-pyrrole-3-carboxylic acid (2-propargyl)-[2'(4-chlorophenyl)phenyl]amide,
1-methoxymethyl-4-trifluoromethyl-1H-pyrrole-3-carboxylic acid (2-acetyl)-[2'(4-fluorophenyl)phenyl]amide,
1-methoxymethyl-4-trifluoromethyl-1H-pyrrole-3-carboxylic acid (2-acetyl)-[2'(4-chlorophenyl)phenyl]amide,
1-methyl-4-trifluoromethyl-1H-pyrrole-3-carboxylic acid (2-methoxyacetyl)-(1,1,3-trimethylindan-4-yl)amide,
1-methyl-4-trifluoromethyl-1H-pyrrole-3-carboxylic acid (2-propargyl)-(1,1,3-trimethylindan-4-yl)amide,
1-methyl-4-trifluoromethyl-1H-pyrrole-3-carboxylic acid (2-acetyl)-(1,1,3-trimethylindan-4-yl)amide,
1-methyl-4-trifluoromethyl-pyrazole-3-carboxylic acid (2-methoxyacetyl)-[2'(4-fluorophenyl)phenyl]amide,
1-methyl-4-trifluoromethyl-pyrazole-3-carboxylic acid (2-methoxyacetyl)-[2'(4-chlorophenyl)phenyl]amide,
1-methyl-4-trifluoromethyl-pyrazole-3-carboxylic acid (2-propargyl)-[2'(4-fluorophenyl)phenyl]amide,
1-methyl-4-trifluoromethyl-pyrazole-3-carboxylic acid (2-propargyl)-[2'(4-chlorophenyl)phenyl]amide,
1-methyl-4-trifluoromethyl-pyrazole-3-carboxylic acid (2-acetyl)-[2'(4-fluorophenyl)phenyl]amide,
1-methyl-4-trifluoromethyl-pyrazole-3-carboxylic acid (2-acetyl)-[2'(4-chlorophenyl)phenyl]amide,
1-methoxymethyl-4-trifluoromethyl-pyrazole-3-carboxylic acid (2-methoxyacetyl)-[2'(4-fluorophenyl)phenyl]amide,
1-methoxymethyl-4-trifluoromethyl-pyrazole-3-carboxylic acid (2-methoxyacetyl)-[2'(4-chlorophenyl)phenyl]amide,
1-methoxymethyl-4-trifluoromethyl-pyrazole-3-carboxylic acid (2-propargyl)-[2'(4-fluorophenyl)phenyl]amide,
1-methoxymethyl-4-trifluoromethyl-pyrazole-3-carboxylic acid (2-propargyl)-[2'(4-chlorophenyl)phenyl]amide,
1-methoxymethyl-4-trifluoromethyl-pyrazole-3-carboxylic acid (2-acetyl)-[2'(4-fluorophenyl)phenyl]amide,
1-methoxymethyl-4-trifluoromethyl-pyrazole-3-carboxylic acid (2-acetyl)-[2'(4-chlorophenyl)phenyl]amide,
1-methyl-4-difluoromethyl-pyrazole-3-carboxylic acid (2-methoxyacetyl)-[2'(4-fluorophenyl)phenyl]amide,
1-methyl-4-difluoromethyl-pyrazole-3-carboxylic acid (2-methoxyacetyl)-[2'(4-chlorophenyl)phenyl]amide,
1-methyl-4-difluoromethyl-pyrazole-3-carboxylic acid (2-propargyl)-[2'(4-fluorophenyl)phenyl]amide,
1-methyl-4-difluoromethyl-pyrazole-3-carboxylic acid (2-propargyl)-[2'(4-chlorophenyl)phenyl]amide,
1-methyl-4-difluoromethyl-pyrazole-3-carboxylic acid (2-acetyl)-[2'(4-fluorophenyl)phenyl]amide, 1-methyl-4-difluoromethyl-pyrazole-3-carboxylic acid (2-acetyl)-[2'(4-chlorophenyl)phenyl]amide,
1-methoxymethyl-4-difluoromethyl-pyrazole-3-carboxylic acid (2-methoxyacetyl)-[2'(4-fluorophenyl)phenyl]amide,
1-methoxymethyl-4-difluoromethyl-pyrazole-3-carboxylic acid (2-methoxyacetyl)-[2'(4-chlorophenyl)phenyl]amide,
1-methoxymethyl-4-difluoromethyl-pyrazole-3-carboxylic acid (2-propargyl)-[2'(4-fluorophenyl)phenyl]amide,
1-methoxymethyl-4-difluoromethyl-pyrazole-3-carboxylic acid (2-propargyl)-[2'(4-chlorophenyl)phenyl]amide,
1-methoxymethyl-4-difluoromethyl-pyrazole-3-carboxylic acid (2-acetyl)-[2'(4-fluorophenyl)phenyl]amide,
1-methoxymethyl-4-difluoromethyl-pyrazole-3-carboxylic acid (2-acetyl)-[2'(4-chlorophenyl)phenyl]amide,
1-methyl-4-trifluoromethyl-thiazole-3-carboxylic acid (2-methoxyacetyl)-[2'(4-fluorophenyl)phenyl]amide,
1-methyl-4-trifluoromethyl-thiazole-3-carboxylic acid (2-methoxyacetyl)-[2'(4-chlorophenyl)phenyl]amide,
1-methyl-4-trifluoromethyl-thiazole-3-carboxylic acid (2-propargyl)-[2'(4-fluorophenyl)phenyl]amide,
1-methyl-4-trifluoromethyl-thiazole-3-carboxylic acid (2-propargyl)-[2'(4-chlorophenyl)phenyl]amide,
1-methyl-4-trifluoromethyl-thiazole-3-carboxylic acid (2-acetyl)-[2'(4-fluorophenyl)phenyl]amide,
1-methyl-4-trifluoromethyl-thiazole-3-carboxylic acid (2-acetyl)-[2'(4-chlorophenyl)phenyl]amide,
1-methyl-4-trifluoromethyl-1H-pyrrole-carboxylic acid (2-methoxyacetyl)-[2'-(3-methylcyclohexyl)phenyl]amide,
1-methyl-4-trifluoromethyl-1H-pyrrole-carboxylic acid (2-methoxyacetyl)-[2'-(3-ethylcyclohexyl)phenyl]amide,
1-methyl-4-trifluoromethyl-1H-pyrrole-carboxylic acid (2-methoxyacetyl)-[2'-(3-trifluoromethylcyclohexyl)phenyl]amide.

The compounds according to formula I may be prepared according to the following reaction scheme.

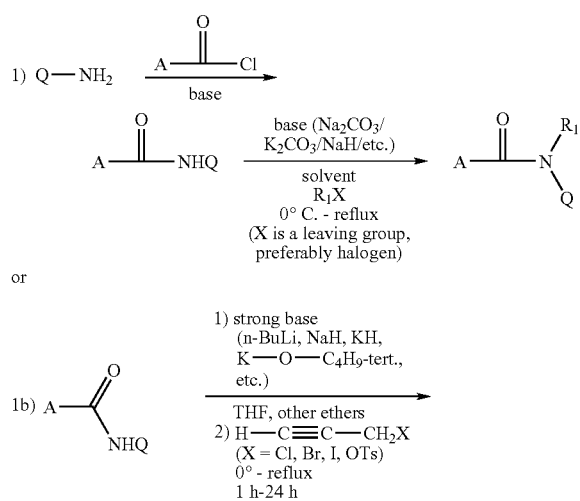

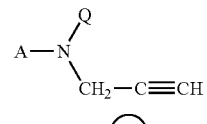

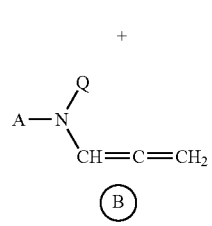

Ratio of product yields A/B depends on reactions conditions (longer reaction time leads to increase of yield of product B) or

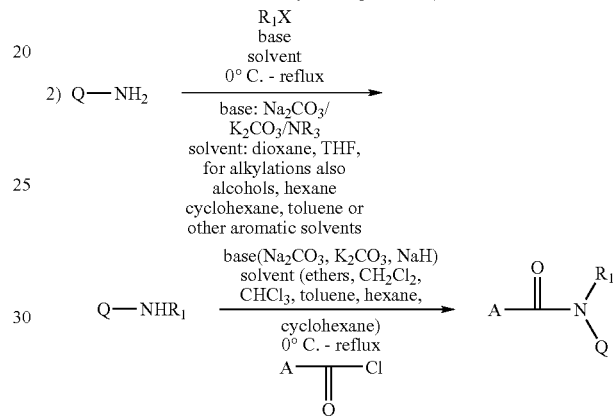

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora,*

*Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present Invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities. Such mixtures are not limited to two active ingredients (one of formula I and one of the list of other fungicides), but to the contrary many comprise more than one active ingredient of the component of formula I and more than one other fungicide. Mixing components which are particularly suited for this purpose include e.g. azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinoles, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofosmethyl; various others, such as acibenzolar-S-methyl, anilazine, benthiavalicarb, blasticidin-S, chinomethionate, chloroneb, chlorothalonil, cyflufenamid, cymoxanil, dichione, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting examples illustrate the above-described invention in more detail. Temperatures are given in degrees Celsius. The following abbreviations are used: m.p.=melting point; b.p.=boiling point. "NMR" means nuclear magnetic resonance spectrum. MS stands for mass spectrum. "%" is percent by weight, unless corresponding concentrations are indicated in other units.

EXAMPLE 1

1-Methyl-4-trifluoromethyl-1H-pyrrole-3-carboxylic acid prop-2-ynyl-(1,1,3-trimethylindan-4-yl)amide

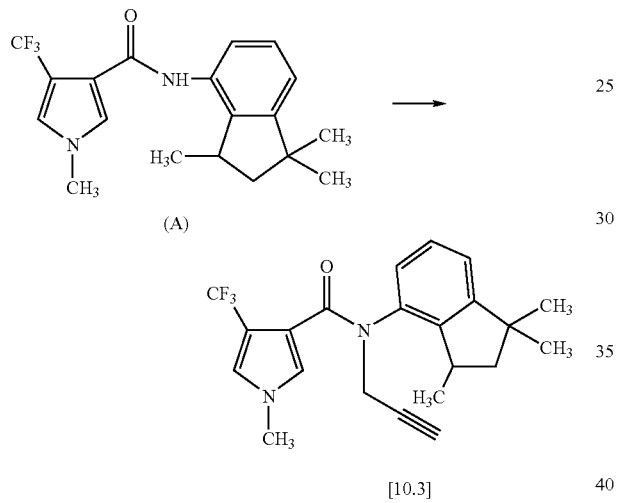

To a solution of 0.49 g (1.4 mmol) of compound (A) in 10 ml tetrahydrofuran is added 67 mg (1.5 mmol) 55%-sodium hydride and the reaction mixture is stirred for 2 hours. Then 0.12 ml (1.6 mmol) propargyl bromide is added and stirring is continued for 1 hour. After addition of ethylacetate, the organic phase is washed once with water and once with sodium chloride solution, dried over sodium sulfate and the solvent is removed. The obtained 1-methyl-4-trifluoromethyl-1H-pyrrole-3-carboxylic acid prop-2-ynyl-(1,1,3-trimethylindan-4-yl)amide (compound 10.3) is recrystallised from dichloromethane/hexane; m.p. 142-144° C.

EXAMPLE 2

1-Methyl-4-trifluoromethyl-1H-pyrrole-3-carboxylic acid (2-methoxyacetyl)-(1,1,3-trimethylindan-4-yl) amide

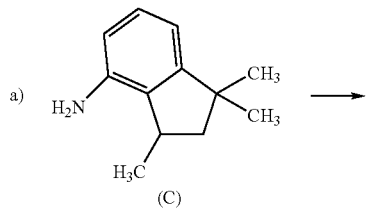

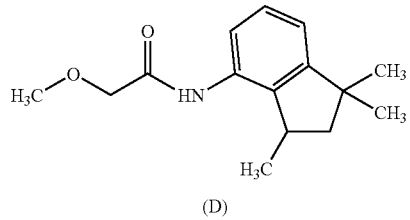

To 1.0 g (5.7 mmol) 4-amino-1,1,3-trimethylindane (C) and 0.63 g (6.3 mmol) triethylamine in 30 ml tetrahydrofuran is added dropwise a solution of 0.65 g (5.9 mmol) methoxyacetyl chloride in 5 ml tetrahydrofuran and the reaction mixture is stirred for 30 minutes. After addition of ethylacetate, the organic phase is washed once with water and once with sodium chloride solution, dried over sodium sulfate and the solvent is removed. It remains 2-methoxy-N-(1,1,3-trimethylindan-4-yl)acetamide (D) as an oil.

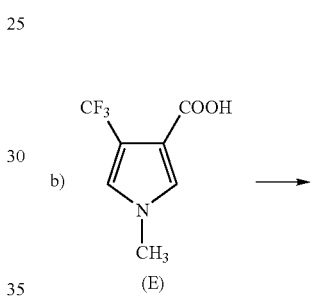

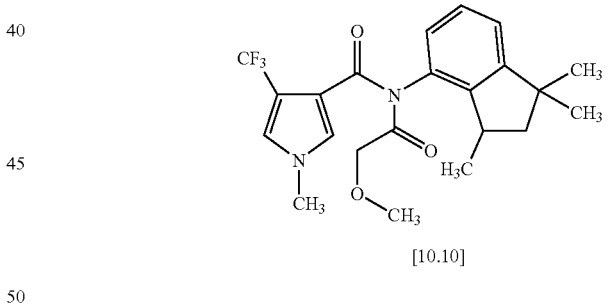

A solution of 0.95 g (4.9 mmol) of compound (E) and 0.68 g (5.4 mmol) oxalylchloride in 25 ml dichloromethane is stirred for 3 hours in the presence of a catalytic amount of dimethylformamide. After removal of the solvent, the acid chloride is slowly added to the solution of 1.23 g (4.9 mmol) of compound (D) and 0.22 g (4.9 mmol) 55%-sodium hydride in 25 ml tetrahydrofuran, which has been stirred for 3 hours. The reaction mixture is stirred for 16 hours. After addition of ethylacetate, the organic phase is washed once with water and once with sodium chloride solution, dried over sodium sulfate and the solvent is removed. Purification by column chromatography over silica gel (eluent hexane: tert.-butylmethylether=7:3) give 1-methyl-4-trifluoromethyl-1H-pyrrole-3-carboxylic acid (2-methoxyacetyl)-(1,1,3-trimethylindan-4-yl)amide (compound 10.10) as a yellow oil.

EXAMPLE 3

1-Methyl-3-trifluoromethyl-1H-pyrazole-4-carboxylic acid (4'-bromobiphenyl-2-yl)prop-2-ynyl-amide (Compd. 2.10) and 1-Methyl-3-trifluoromethyl-1H-pyrazole-4-carboxylic acid (4'-bromobiphenyl-2-yl)propa-1,2-dienyl-amide (Compd. 2.123)

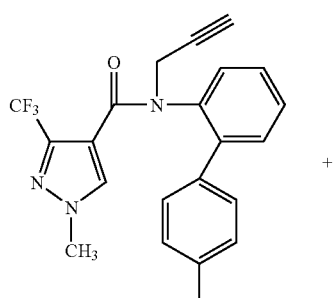

Compd. 2.10

+

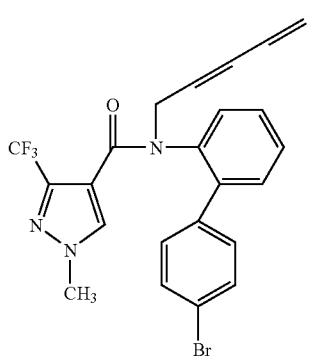

Compd. 2.123

To a mixture of 137 mg 3.15 mmol sodiumhydride (~60%) and 15 ml of absolute THF a solution of 1.27 g (3.0 mmol) of 1-methyl-3-trifluoromethyl-1H-pyrazole-4-carboxylic acid (4'-bromobiphenyl-2-yl)amide is added slowly and stirred for 20 minutes at +45° C. Then the solution is coold to +20° C. and 410 mg (3.45 mmol) of 3-bromo-1-propyne in 10 ml of THF added slowly. The resulting mixture is stirred for 20 hours and then 100 ml of ice water is added. The ethylacetate is added and the water phase extracted three times with ethylacetate. After drying of the combined organic phase and evaporation of the solvent in a water jet vacuum the crude product is obtained. The separation of compounds. 2.10 and 2.123 is accomplished via column chromatography over silicagel (eluent: hexane/CH$_2$Cl$_2$/isoproplyether 1:1:1). Compound. 2.123 is obtained in the form of a white powder: m.p. 146-149° C. and compound. 2.10 is obtained in the form of a white powder: m.p. 171-172° C.

In analogous manner the compounds of the following tables are obtained.

TABLE 1

Intermediates

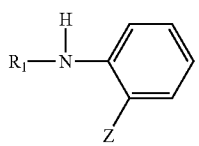

(II)

| Cmpd. no. | R$_1$ | Z | phys. data m.p. ° C. |
|---|---|---|---|
| 1.01 | —CH$_2$CH=CH$_2$ | 4-F-phenyl | |
| 1.02 | —CH$_2$CH=CH$_2$ | 4-Cl-phenyl | |
| 1.03 | —CH$_2$CH=CH$_2$ | 4-Br-phenyl | |
| 1.04 | —CH$_2$CH=CH$_2$ | 3-Me-cyclopentyl | |
| 1.05 | —CH$_2$CH=CH$_2$ | 4-Me-cyclohexyl | |
| 1.06 | —CH$_2$CH=CH$_2$ | 3-Me-cyclohexyl | |
| 1.07 | —CH$_2$CH=CH$_2$ | cycloheptyl | |
| 1.08 | —CH$_2$CH=CH$_2$ | (CH$_3$)$_2$CHCH$_2$CH(CH$_3$)— | |
| 1.09 | —CH$_2$C≡CH | 4-F-phenyl | |
| 1.10 | —CH$_2$C≡CH | 4-Cl-phenyl | |
| 1.11 | —CH$_2$C≡CH | 4-Br-phenyl | |
| 1.12 | —CH$_2$C≡CH | 3-Me-cyclopentyl | |
| 1.13 | —CH$_2$C≡CH | 4-Me-cyclohexyl | |
| 1.14 | —CH$_2$C≡CH | 3-Me-cyclohexyl | |
| 1.15 | —CH$_2$C≡CH | cycloheptyl | |
| 1.16 | —CH$_2$C≡CH | (CH$_3$)$_2$CHCH$_2$CH(CH$_3$)— | |
| 1.17 | —COCH$_3$ | 4-F-phenyl | |
| 1.18 | —COCH$_3$ | 4-Cl-phenyl | |
| 1.19 | —COCH$_3$ | 4-Br-phenyl | |
| 1.20 | —COCH$_3$ | 3-Me-cyclopentyl | |
| 1.21 | —COCH$_3$ | 4-Me-cyclohexyl | |
| 1.22 | —COCH$_3$ | 3-Me-cyclohexyl | |
| 1.23 | —COCH$_3$ | cycloheptyl | |
| 1.24 | —COCH$_3$ | (CH$_3$)$_2$CHCH$_2$CH(CH$_3$)— | 84-86 |
| 1.25 | —COCH$_2$CH$_3$ | 4-F-phenyl | |
| 1.26 | —COCH$_2$CH$_3$ | 4-Cl-phenyl | |
| 1.27 | —COCH$_2$CH$_3$ | 4-br-phenyl | |
| 1.28 | —COCH$_2$CH$_3$ | 3-Me-cyclopentyl | |
| 1.29 | —COCH$_2$CH$_3$ | 4-Me-cyclohexyl | |
| 1.30 | —COCH$_2$CH$_3$ | 3-Me-cyclohexyl | |
| 1.31 | —COCH$_2$CH$_3$ | cycloheptyl | |
| 1.32 | —COCH$_2$CH$_3$ | (CH$_3$)$_2$CHCH$_2$CH(CH$_3$)— | |
| 1.33 | —COCH$_2$CH$_2$CH$_3$ | 4-F-phenyl | |
| 1.34 | —COCH$_2$CH$_2$CH$_3$ | 4-Cl-phenyl | |
| 1.35 | —COCH$_2$CH$_2$CH$_3$ | 4-Br-phenyl | |
| 1.36 | —COCH$_2$CH$_2$CH$_3$ | cycloheptyl | |
| 1.37 | —COCH$_2$CH$_2$CH$_3$ | (CH$_3$)$_2$CHCH$_2$CH(CH$_3$)— | |
| 1.38 | —COcyclopropyl | 4-F-phenyl | |
| 1.39 | —COcyclopropyl | 4-Cl-phenyl | |

TABLE 1-continued

Intermediates

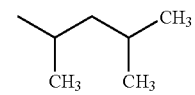
(II)

| Cmpd. no. | R₁ | Z | phys. data m.p. °C. |
|---|---|---|---|
| 1.40 | —COcyclopropyl | 4-Br-phenyl | |
| 1.41 | —COcyclopropyl | cycloheptyl | |
| 1.42 | —COcyclopropyl | (CH₃)₂CHCH₂CH(CH₃) | |
| 1.43 | —COCH₂OCH₃ | 4-F-phenyl | |
| 1.44 | —COCH₂OCH₃ | 4-Cl-phenyl | |
| 1.45 | —COCH₂OCH₃ | 4-Br-phenyl | |
| 1.46 | —COCH₂OCH₃ | 3-Me-cyclopentyl | |
| 1.47 | —COCH₂OCH₃ | 4-Me-cyclohexyl | |
| 1.48 | —COCH₂OCH₃ | 3-Me-cyclohexyl | |
| 1.49 | —COCH₂OCH₃ | cycloheptyl | |
| 1.50 | —COCH₂OCH₃ | (CH₃)₂CHCH₂CH(CH₃) | resin; $M^+ = 249$ |
| 1.51 | —COCH₂OCH₂CH₃ | 4-F-phenyl | |
| 1.52 | —COCH₂OCH₂CH₃ | 4-Cl-phenyl | |
| 1.53 | —COCH₂OCH₂CH₃ | 4-Br-phenyl | |
| 1.54 | —COCH₂OCH₂CH₃ | cycloheptyl | |

TABLE 1-continued

Intermediates

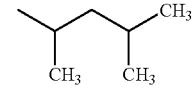
(II)

| Cmpd. no. | R₁ | Z | phys. data m.p. °C. |
|---|---|---|---|
| 1.55 | —COCH₂OCH₂CH₃ | (CH₃)₂CHCH₂CH(CH₃) | |
| 1.56 | —COOCH₃ | 4-F-phenyl | |
| 1.57 | —COOCH₃ | 4-Cl-phenyl | |
| 1.58 | —COOCH₃ | 4-Br-phenyl | |
| 1.59 | —COOCH₃ | 3-Me-cyclopentyl | |
| 1.60 | —COOCH₃ | 4-Me-cyclohexyl | |
| 1.61 | —COOCH₃ | 3-Me-cyclohexyl | |
| 1.62 | —COOCH₃ | cycloheptyl | |
| 1.63 | —COOCH₃ | (CH₃)₂CHCH₂CH(CH₃) | |

TABLE 2

Pyrazolecarboxamides

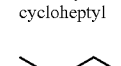
(Ia)

| Cmpd. no. | R₁ | R₄ | R₅ | R₆ | Z | phys. data m.p. °C. |
|---|---|---|---|---|---|---|
| 2.001 | —CH₂CH=CH₂ | —CF₃ | —CH₃ | H | 4-Cl-phenyl | 93-95 |
| 2.002 | —CH₂CH=CH₂ | —CF₃ | —CH₃ | H | 4-Br-phenyl | |
| 2.003 | —CH₂CH=CH₂ | —CF₃ | —CH₃ | H | 3-Me-cyclopentyl | |
| 2.004 | —CH₂CH=CH₂ | —CF₃ | —CH₃ | H | 4-Me-cyclohexyl | |
| 2.005 | —CH₂CH=CH₂ | —CF₃ | —CH₃ | H | 3-Me-cyclohexyl | |
| 2.006 | —CH₂CH=CH₂ | —CF₃ | —CH₃ | H | cycloheptyl | |
| 2.007 | —CH₂CH=CH₂ | —CF₃ | —CH₃ | H | (CH₃)₂CHCH₂CH(CH₃) | 73-75 |
| 2.008 | —CH₂C≡CH | —CF₃ | —CH₃ | H | 4-F-phenyl | |
| 2.009 | —CH₂C≡CH | —CF₃ | —CH₃ | H | 4-Cl-phenyl | 169-170 $M^+ = 415$ |
| 2.010 | —CH₂C≡CH | —CF₃ | —CH₃ | H | 4-Br-phenyl | 171-172 |
| 2.011 | —CH₂C≡CH | —CF₃ | —CH₃ | H | 3-Me-cyclopentyl | |

TABLE 2-continued

Pyrazolecarboxamides

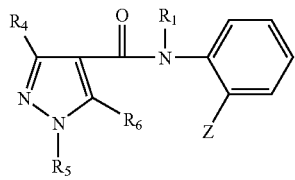

(Ia)

| Cmpd. no. | R$_1$ | R$_4$ | R$_5$ | R$_6$ | Z | phys. data m.p. ° C. |
|---|---|---|---|---|---|---|
| 2.012 | —CH$_2$C≡CH | —CF$_3$ | —CH$_3$ | H | 4-Me-cyclohexyl | |
| 2.013 | —CH$_2$C≡CH | —CF$_3$ | —CH$_3$ | H | 3-Me-cyclohexyl | |
| 2.014 | —CH$_2$C≡CH | —CF$_3$ | —CH$_3$ | H | cycloheptyl | |
| 2.015 | —CH$_2$C≡CH | —CF$_3$ | —CH$_3$ | H | (CH$_3$)$_2$CHCH$_2$CH(CH$_3$)— | 100-102 |
| 2.016 | —CH$_2$C≡CH | —CF$_2$H | —CH$_3$ | H | 4-F-phenyl | 127-128 |
| 2.017 | —CH$_2$C≡CH | —CF$_2$H | —CH$_3$ | H | 4-Cl-phenyl | 151-152 |
| 2.018 | —CH$_2$C≡CH | —CF$_2$H | —CH$_3$ | H | 3-Me-cyclopentyl | |
| 2.019 | —CH$_2$C≡CH | —CF$_2$H | —CH$_3$ | H | 4-Me-cyclohexyl | |
| 2.020 | —CH$_2$C≡CH | —CF$_2$H | —CH$_3$ | H | 3-Me-cyclohexyl | |
| 2.021 | —CH$_2$C≡CH | —CF$_2$H | —CH$_3$ | H | cycloheptyl | |
| 2.022 | —CH$_2$C≡CH | —CF$_2$H | —CH$_3$ | H | (CH$_3$)$_2$CHCH$_2$CH(CH$_3$)— | |
| 2.023 | —CH$_2$C≡CH | —CF$_3$ | —CH$_2$OCH$_3$ | H | 4-F-phenyl | |
| 2.024 | —CH$_2$C≡CH | —CF$_3$ | —CH$_2$OCH$_3$ | H | 4-Cl-phenyl | |
| 2.025 | —CH$_2$C≡CH | —CF$_3$ | —CH$_2$OCH$_3$ | H | 3-Me-cyclopentyl | |
| 2.026 | —CH$_2$C≡CH | —CF$_3$ | —CH$_2$OCH$_3$ | H | 3-Me-cyclohexyl | |
| 2.027 | —CH$_2$C≡CH | —CF$_3$ | —CH$_2$OCH$_3$ | H | cycloheptyl | |
| 2.028 | —CH$_2$C≡CH | —CF$_3$ | —CH$_2$OCH$_3$ | H | (CH$_3$)$_2$CHCH$_2$CH(CH$_3$)— | |
| 2.029 | —CH$_2$C≡CH | —CF$_3$ | —CH$_3$ | F | 4-F-phenyl | |
| 2.030 | —CH$_2$C≡CH | —CF$_3$ | —CH$_3$ | F | 4-Cl-phenyl | |
| 2.031 | —CH$_2$C≡CH | —CF$_3$ | —CH$_3$ | F | 3-Me-cyclopentyl | |
| 2.032 | —CH$_2$C≡CH | —CF$_3$ | —CH$_3$ | F | 3-Me-cyclohexyl | |
| 2.033 | —CH$_2$C≡CH | —CF$_3$ | —CH$_3$ | F | cycloheptyl | |
| 2.034 | —CH$_2$C≡CH | —CF$_3$ | —CH$_3$ | F | (CH$_3$)$_2$CHCH$_2$CH(CH$_3$)— | |
| 2.035 | —COCH$_3$ | —CF$_3$ | —CH$_3$ | H | 4-F-phenyl | |
| 2.036 | —COCH$_3$ | —CF$_3$ | —CH$_3$ | H | 4-Cl-phenyl | |
| 2.037 | —COCH$_3$ | —CF$_3$ | —CH$_3$ | H | 4-Br-phenyl | |
| 2.038 | —COCH$_3$ | —CF$_3$ | —CH$_3$ | H | 3-Me-cyclopentyl | |
| 2.039 | —COCH$_3$ | —CF$_3$ | —CH$_3$ | H | 4-Me-cyclohexyl | |
| 2.040 | —COCH$_3$ | —CF$_3$ | —CH$_3$ | H | 3-Me-cyclohexyl | |
| 2.041 | —COCH$_3$ | —CF$_3$ | —CH$_3$ | H | cycloheptyl | |
| 2.042 | —COCH$_3$ | —CF$_3$ | —CH$_3$ | H | (CH$_3$)$_2$CHCH$_2$CH(CH$_3$)— | 95-97 |
| 2.043 | —COCH$_3$ | —CF$_2$H | —CH$_3$ | H | 4-F-phenyl | |
| 2.044 | —COCH$_3$ | —CF$_2$H | —CH$_3$ | H | 4-Cl-phenyl | |
| 2.045 | —COCH$_3$ | —CF$_2$H | —CH$_3$ | H | 3-Me-cyclopentyl | |
| 2.046 | —COCH$_3$ | —CF$_2$H | —CH$_3$ | H | 3-Me-cyclohexyl | |
| 2.047 | —COCH$_3$ | —CF$_2$H | —CH$_3$ | H | cycloheptyl | |

TABLE 2-continued

Pyrazolecarboxamides (Ia)

| Cmpd. no. | $R_1$ | $R_4$ | $R_5$ | $R_6$ | Z | phys. data m.p. ° C. |
|---|---|---|---|---|---|---|
| 2.048 | —COCH$_3$ | —CF$_2$H | —CH$_3$ | H | (CH$_3$)$_2$CHCH$_2$CH(CH$_3$)— | |
| 2.049 | —COCH$_3$ | —CF$_3$ | —CH$_2$OCH$_3$ | H | 4-F-phenyl | |
| 2.050 | —COCH$_3$ | —CF$_3$ | —CH$_2$OCH$_3$ | H | 4-Cl-phenyl | |
| 2.051 | —COCH$_3$ | —CF$_3$ | —CH$_2$OCH$_3$ | H | 3-Me-cyclopentyl | |
| 2.052 | —COCH$_3$ | —CF$_3$ | —CH$_2$OCH$_3$ | H | 3-Me-cyclohexyl | |
| 2.053 | —COCH$_3$ | —CF$_3$ | —CH$_2$OCH$_3$ | H | cycloheptyl | |
| 2.054 | —COCH$_3$ | —CF$_3$ | —CH$_2$OCH$_3$ | H | (CH$_3$)$_2$CHCH$_2$CH(CH$_3$)— | |
| 2.055 | —COCH$_3$ | —CF$_3$ | —CH$_3$ | F | 4-F-phenyl | |
| 2.056 | —COCH$_3$ | —CF$_3$ | —CH$_3$ | F | 4-Cl-phenyl | resin; M$^+$ = 421($^{35}$Cl) |
| 2.057 | —COCH$_3$ | —CF$_3$ | —CH$_3$ | F | 4-Br-phenyl | |
| 2.058 | —COCH$_3$ | —CF$_3$ | —CH$_3$ | F | 3-Me-cyclohexyl | |
| 2.059 | —COCH$_3$ | —CF$_3$ | —CH$_3$ | F | cycloheptyl | |
| 2.060 | —COCH$_3$ | —CF$_3$ | —CH$_3$ | F | (CH$_3$)$_2$CHCH$_2$CH(CH$_3$)— | |
| 2.061 | —COCH$_2$CH$_3$ | —CF$_3$ | —CH$_3$ | H | 4-F-phenyl | |
| 2.062 | —COCH$_2$CH$_3$ | —CF$_3$ | —CH$_3$ | H | 4-Cl-phenyl | resin; M$^+$ = 435($^{35}$Cl) |
| 2.063 | —COCH$_2$CH$_3$ | —CF$_3$ | —CH$_3$ | H | 4-Br-phenyl | |
| 2.064 | —COCH$_2$CH$_3$ | —CF$_3$ | —CH$_3$ | H | 3-Me-cyclopentyl | |
| 2.065 | —COCH$_2$CH$_3$ | —CF$_3$ | —CH$_3$ | H | 4-Me-cyclohexyl | |
| 2.066 | —COCH$_2$CH$_3$ | —CF$_3$ | —CH$_3$ | H | 3-Me-cyclohexyl | |
| 2.067 | —COCH$_2$CH$_3$ | —CF$_3$ | —CH$_3$ | H | cycloheptyl | |
| 2.068 | —COCH$_2$CH$_3$ | —CF$_3$ | —CH$_3$ | H | (CH$_3$)$_2$CHCH$_2$CH(CH$_3$)— | 92-94 |
| 2.069 | —COCH$_2$CH$_3$ | —CF$_3$ | —CH$_3$ | H | 4-F-phenyl | |
| 2.070 | —COCH$_2$CH$_3$ | —CF$_2$H | —CH$_3$ | H | 4-Cl-phenyl | |
| 2.071 | —COCH$_2$CH$_3$ | —CF$_2$H | —CH$_3$ | H | 4-Br-phenyl | |
| 2.072 | —COCH$_2$CH$_3$ | —CF$_2$H | —CH$_3$ | H | cycloheptyl | |
| 2.073 | —COCH$_2$CH$_3$ | —CF$_2$H | —CH$_3$ | H | (CH$_3$)$_2$CHCH$_2$CH(CH$_3$)— | |
| 2.074 | —COCH$_2$CH$_2$CH$_3$ | —CF$_3$ | —CH$_3$ | H | 4-F-phenyl | |
| 2.075 | —COCH$_2$CH$_2$CH$_3$ | —CF$_3$ | —CH$_3$ | H | 4-Cl-phenyl | resin; M$^+$ = |
| 2.076 | —COCH$_2$CH$_2$CH$_3$ | —CF$_3$ | —CH$_3$ | H | 4-Br-phenyl | |
| 2.077 | —COCH$_2$CH$_2$CH$_3$ | —CF$_3$ | —CH$_3$ | H | cycloheptyl | |
| 2.078 | —COCH$_2$CH$_2$CH$_3$ | —CF$_3$ | —CH$_3$ | H | (CH$_3$)$_2$CHCH$_2$CH(CH$_3$)— | |

TABLE 2-continued

Pyrazolecarboxamides

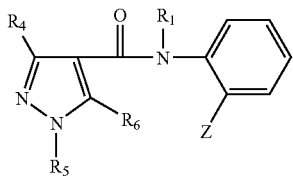

(Ia)

| Cmpd. no. | R₁ | R₄ | R₅ | R₆ | Z | phys. data m.p. ° C. |
|---|---|---|---|---|---|---|
| 2.079 | —COcyclopropyl | —CF₃ | —CH₃ | H | 4-F-phenyl | |
| 2.080 | —COcyclopropyl | —CF₃ | —CH₃ | H | 4-Cl-phenyl | |
| 2.081 | —COcyclopropyl | —CF₃ | —CH₃ | H | 4-Br-phenyl | |
| 2.082 | —COcyclopropyl | —CF₃ | —CH₃ | H | cycloheptyl | |
| 2.083 | —COcyclopropyl | —CF₃ | —CH₃ | H | (CH(CH₃)CH₂CH(CH₃)₂) | |
| 2.084 | —COCH₂OCH₃ | —CF₃ | —CH₃ | H | 4-F-phenyl | |
| 2.085 | —COCH₂OCH₃ | —CF₃ | —CH₃ | H | 4-Cl-phenyl | 55-57 |
| 2.086 | —COCH₂OCH₃ | —CF₃ | —CH₃ | H | 4-Br-phenyl | |
| 2.087 | —COCH₂OCH₃ | —CF₃ | —CH₃ | H | 3-Me-cyclopentyl | |
| 2.088 | —COCH₂OCH₃ | —CF₃ | —CH₃ | H | 4-Me-cyclohexyl | |
| 2.089 | —COCH₂OCH₃ | —CF₃ | —CH₃ | H | 3-Me-cyclohexyl | |
| 2.090 | —COCH₂OCH₃ | —CF₃ | —CH₃ | H | cycloheptyl | |
| 2.091 | —COCH₂OCH₃ | —CF₃ | —CH₃ | H | (CH(CH₃)CH₂CH(CH₃)₂) | resin; M⁺ = 425 |
| 2.092 | —COCH₂OCH₃ | —CF₂H | —CH₃ | H | 4-F-phenyl | |
| 2.093 | —COCH₂OCH₃ | —CF₂H | —CH₃ | H | 4-F-phenyl | |
| 2.094 | —COCH₂OCH₃ | —CF₂H | —CH₃ | H | 4-Cl-phenyl | |
| 2.095 | —COCH₂OCH₃ | —CF₂H | —CH₃ | H | 4-Br-phenyl | |
| 2.096 | —COCH₂OCH₃ | —CF₂H | —CH₃ | H | cycloheptyl | |
| 2.097 | —COCH₂OCH₃ | —CF₂H | —CH₃ | H | (CH(CH₃)CH₂CH(CH₃)₂) | |
| 2.098 | —COCH₂OCH₃ | —CF₃ | —CH₃ | F | 4-Cl-phenyl | |
| 2.099 | —COCH₂OCH₂CH₃ | —CF₃ | —CH₃ | H | 4-F-phenyl | |
| 2.100 | —COCH₂OCH₂CH₃ | —CF₃ | —CH₃ | H | 4-Cl-phenyl | |
| 2.101 | —COCH₂OCH₂CH₃ | —CF₃ | —CH₃ | H | 4-Br-phenyl | |
| 2.102 | —COCH₂OCH₂CH₃ | —CF₃ | —CH₃ | H | 3-Me-cyclohexyl | |
| 2.103 | —COCH₂OCH₂CH₃ | —CF₃ | —CH₃ | H | cycloheptyl | |
| 2.104 | —COCH₂OCH₂CH₃ | —CF₃ | —CH₃ | H | (CH(CH₃)CH₂CH(CH₃)₂) | |
| 2.105 | —COOCH₃ | —CF₃ | —CH₃ | H | 4-F-phenyl | |
| 2.106 | —COOCH₃ | —CF₃ | —CH₃ | H | 4-Cl-phenyl | |
| 2.107 | —COOCH₃ | —CF₃ | —CH₃ | H | 4-Br-phenyl | |
| 2.108 | —COOCH₃ | —CF₃ | —CH₃ | H | 3-Me-cyclopentyl | |
| 2.109 | —COOCH₃ | —CF₃ | —CH₃ | H | 4-Me-cyclohexyl | |
| 2.110 | —COOCH₃ | —CF₃ | —CH₃ | H | 3-Me-cyclohexyl | |
| 2.111 | —COOCH₃ | —CF₃ | —CH₃ | H | cycloheptyl | |
| 2.112 | —COOCH₃ | —CF₃ | —CH₃ | H | (CH(CH₃)CH₂CH(CH₃)₂) | |
| 2.113 | —COOCH₃ | —CF₂H | —CH₃ | H | 4-F-phenyl | |
| 2.114 | —COOCH₃ | —CF₂H | —CH₃ | H | 4-Cl-phenyl | |

TABLE 2-continued

Pyrazolecarboxamides

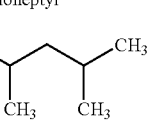

(Ia)

| Cmpd. no. | R$_1$ | R$_4$ | R$_5$ | R$_6$ | Z | phys. data m.p. ° C. |
|---|---|---|---|---|---|---|
| 2.115 | —COOCH$_3$ | —CF$_2$H | —CH$_3$ | H | 4-Br-phenyl | |
| 2.116 | —COOCH$_3$ | —CF$_2$H | —CH$_3$ | H | cycloheptyl | |
| 2.117 | —COOCH$_3$ | —CF$_2$H | —CH$_3$ | H | 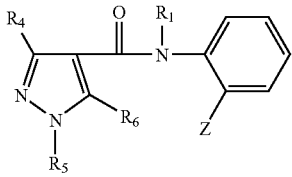 | |
| 2.118 | —COOCH$_3$ | —CF$_3$ | —CH$_3$ | F | 4-F-phenyl | |
| 2.119 | —COOCH$_3$ | —CF$_3$ | —CH$_3$ | F | 4-Cl-phenyl | |
| 2.120 | —COOCH$_3$ | —CF$_3$ | —CH$_3$ | F | cycloheptyl | |
| 2.121 | —CH=C=CH$_2$ | —CF$_3$ | —CH$_3$ | H | 4-F-phenyl | |
| 2.122 | —CH=C=CH$_2$ | —CF$_3$ | —CH$_3$ | H | 4-Cl-phenyl | 144-146 |
| 2.123 | —CH=C=CH$_2$ | —CF$_3$ | —CH$_3$ | H | 4-Br-phenyl | 146-149 |
| 2.124 | —CH=C=CH$_2$ | —CF$_2$H | —CH$_3$ | H | 4-F-phenyl | 148-149 |
| 2.125 | —CH=C=CH$_2$ | —CF$_2$H | —CH$_3$ | H | 4-Cl-phenyl | 157-159 |
| 2.126 | —CH=C=CH$_2$ | —CF$_2$H | —CH$_3$ | H | 4-Br-phenyl | 163-164 |

TABLE 3

Pyrrolecarboxamides (Ib)

| Cmpd. no. | R$_1$ | R$_4$ | R$_5$ | R$_6$ | Z | phys. data m.p. ° C. |
|---|---|---|---|---|---|---|
| 3.01 | —CH$_2$CH=CH$_2$ | —CF$_3$ | —CH$_3$ | H | 4-F-phenyl | resin; M$^+$ = 402 |
| 3.02 | —CH$_2$CH=CH$_2$ | —CF$_3$ | —CH$_3$ | H | 4-Br-phenyl | |
| 3.03 | —CH$_2$CH=CH$_2$ | —CF$_3$ | —CH$_3$ | H | 3-Me-cyclopentyl | |
| 3.04 | —CH$_2$CH=CH$_2$ | —CF$_3$ | —CH$_3$ | H | 4-Me-cyclohexyl | |
| 3.05 | —CH$_2$CH=CH$_2$ | —CF$_3$ | —CH$_3$ | H | 3-Me-cyclohexyl | |
| 3.06 | —CH$_2$CH=CH$_2$ | —CF$_3$ | —CH$_3$ | H | cycloheptyl | |
| 3.07 | —CH$_2$CH=CH$_2$ | —CF$_3$ | —CH$_3$ | H | 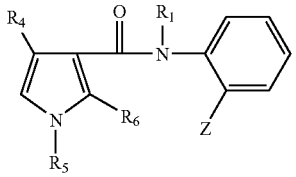 | |
| 3.08 | —CH$_2$C≡CH | —CF$_3$ | —CH$_3$ | H | 4-F-phenyl | 109-112 |
| 3.09 | —CH$_2$C≡CH | —CF$_3$ | —CH$_3$ | H | 4-Cl-phenyl | |
| 3.10 | —CH$_2$C≡CH | —CF$_3$ | —CH$_3$ | H | 4-Br-phenyl | 130-131 |
| 3.11 | —CH$_2$C≡CH | —CF$_3$ | —CH$_3$ | H | 3-Me-cyclopentyl | |
| 3.12 | —CH$_2$C≡CH | —CF$_3$ | —CH$_3$ | H | 4-Me-cyclohexyl | |
| 3.13 | —CH$_2$C≡CH | —CF$_3$ | —CH$_3$ | H | 3-Me-cyclohexyl | |
| 3.14 | —CH$_2$C≡CH | —CF$_3$ | —CH$_3$ | H | cycloheptyl | |
| 3.15 | —CH$_2$C≡CH | —CF$_3$ | —CH$_3$ | H | | |

TABLE 3-continued

Pyrrolecarboxamides

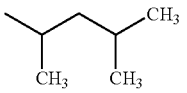

(Ib)

| Cmpd. no. | R₁ | R₄ | R₅ | R₆ | Z | phys. data m.p. ° C. |
|---|---|---|---|---|---|---|
| 3.16 | —CH₂C≡CH | —CF₃ | —CH₂OCH₃ | H | 4-F-phenyl | |
| 3.17 | —CH₂C≡CH | —CF₃ | —CH₂OCH₃ | H | 4-Cl-phenyl | |
| 3.18 | —CH₂C≡CH | —CF₃ | —CH₂OCH₃ | H | 3-Me-cyclopentyl | |
| 3.19 | —CH₂C≡CH | —CF₃ | —CH₂OCH₃ | H | 3-Me-cyclohexyl | |
| 3.20 | —CH₂C≡CH | —CF₃ | —CH₂OCH₃ | H | cycloheptyl | |
| 3.21 | —CH₂C≡CH | —CF₃ | —CH₂OCH₃ | H | 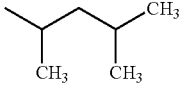 | |
| 3.22 | —CH₂C≡CH | —CF₃ | —CH₃ | F | 4-F-phenyl | |
| 3.23 | —CH₂C≡CH | —CF₃ | —CH₃ | F | 4-Cl-phenyl | |
| 3.24 | —CH₂C≡CH | —CF₃ | —CH₃ | F | 3-Me-cyclopentyl | |
| 3.25 | —CH₂C≡CH | —CF₃ | —CH₃ | F | 3-Me-cyclohexyl | |
| 3.26 | —CH₂C≡CH | —CF₃ | —CH₃ | F | cycloheptyl | |
| 3.27 | —CH₂C≡CH | —CF₃ | —CH₃ | F | 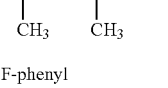 | |
| 3.28 | —COCH₃ | —CF₃ | —CH₃ | H | 4-F-phenyl | resin; M⁺ = 404 |
| 3.29 | —COCH₃ | —CF₃ | —CH₃ | H | 4-Cl-phenyl | |
| 3.30 | —COCH₃ | —CF₃ | —CH₃ | H | 4-Br-phenyl | |
| 3.31 | —COCH₃ | —CF₃ | —CH₃ | H | 3-Me-cyclopentyl | |
| 3.32 | —COCH₃ | —CF₃ | —CH₃ | H | 4-Me-cyclohexyl | |
| 3.33 | —COCH₃ | —CF₃ | —CH₃ | H | 3-Me-cyclohexyl | |
| 3.34 | —COCH₃ | —CF₃ | —CH₃ | H | cycloheptyl | |
| 3.35 | —COCH₃ | —CF₃ | —CH₃ | H | 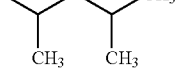 | |
| 3.36 | —COCH₃ | —CF₃ | —CH₂OCH₃ | H | 4-F-phenyl | |
| 3.37 | —COCH₃ | —CF₃ | —CH₂OCH₃ | H | 4-Cl-phenyl | |
| 3.38 | —COCH₃ | —CF₃ | —CH₂OCH₃ | H | 3-Me-cyclopentyl | |
| 3.39 | —COCH₃ | —CF₃ | —CH₂OCH₃ | H | 3-Me-cyclohexyl | |
| 3.40 | —COCH₃ | —CF₃ | —CH₂OCH₃ | H | cycloheptyl | |
| 3.41 | —COCH₃ | —CF₃ | —CH₂OCH₃ | H | 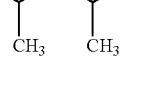 | |
| 3.42 | —COCH₃ | —CF₃ | —CH₃ | F | 4-F-phenyl | |
| 3.43 | —COCH₃ | —CF₃ | —CH₃ | F | 4-Cl-phenyl | |
| 3.44 | —COCH₃ | —CF₃ | —CH₃ | F | 3-Me-cyclopentyl | |
| 3.45 | —COCH₃ | —CF₃ | —CH₃ | F | 3-Me-cyclohexyl | |
| 3.46 | —COCH₃ | —CF₃ | —CH₃ | F | cycloheptyl | |
| 3.47 | —COCH₃ | —CF₃ | —CH₃ | F |  | |
| 3.48 | —COCH₂CH₃ | —CF₃ | —CH₃ | H | 4-F-phenyl | |
| 3.49 | —COCH₂CH₃ | —CF₃ | —CH₃ | H | 4-Cl-phenyl | |
| 3.50 | —COCH₂CH₃ | —CF₃ | —CH₃ | H | 4-Br-phenyl | |

TABLE 3-continued

Pyrrolecarboxamides

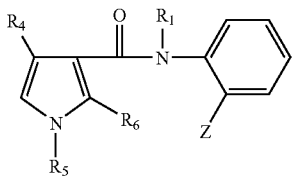

(Ib)

| Cmpd. no. | $R_1$ | $R_4$ | $R_5$ | $R_6$ | Z | phys. data m.p. ° C. |
|---|---|---|---|---|---|---|
| 3.51 | —COCH₂CH₃ | —CF₃ | —CH₃ | H | 3-Me-cyclopentyl | |
| 3.52 | —COCH₂CH₃ | —CF₃ | —CH₃ | H | 4-Me-cyclohexyl | |
| 3.53 | —COCH₂CH₃ | —CF₃ | —CH₃ | H | 3-Me-cyclohexyl | |
| 3.54 | —COCH₂CH₃ | —CF₃ | —CH₃ | H | cycloheptyl | |
| 3.55 | —COCH₂CH₃ | —CF₃ | —CH₃ | H | 2,4-dimethylpentan-3-yl | |
| 3.56 | —COCH₂CH₃ | —CF₃ | —CH₃ | H | 4-F-phenyl | |
| 3.57 | —COCH₂CH₂CH₃ | —CF₃ | —CH₃ | H | 4-F-phenyl | |
| 3.58 | —COCH₂CH₂CH₃ | —CF₃ | —CH₃ | H | 4-Cl-phenyl | |
| 3.59 | —COCH₂CH₂CH₃ | —CF₃ | —CH₃ | H | 4-Br-phenyl | |
| 3.60 | —COCH₂CH₂CH₃ | —CF₃ | —CH₃ | H | cycloheptyl | |
| 3.61 | —COCH₂CH₂CH₃ | —CF₃ | —CH₃ | H | 2,4-dimethylpentan-3-yl | resin; $M^+ = 422$ |
| 3.62 | —COcyclopropyl | —CF₃ | —CH₃ | H | 4-F-phenyl | |
| 3.63 | —COcyclopropyl | —CF₃ | —CH₃ | H | 4-Cl-phenyl | |
| 3.64 | —COcyclopropyl | —CF₃ | —CH₃ | H | 4-Br-phenyl | |
| 3.65 | —COcyclopropyl | —CF₃ | —CH₃ | H | cycloheptyl | |
| 3.66 | —COcyclopropyl | —CF₃ | —CH₃ | H | 2,4-dimethylpentan-3-yl | |
| 3.67 | —COCH₂OCH₃ | —CF₃ | —CH₃ | H | 4-F-phenyl | resin; $M^+ = 434$ |
| 3.68 | —COCH₂OCH₃ | —CF₃ | —CH₃ | H | 4-Cl-phenyl | |
| 3.69 | —COCH₂OCH₃ | —CF₃ | —CH₃ | H | 4-Br-phenyl | |
| 3.70 | —COCH₂OCH₃ | —CF₃ | —CH₃ | H | 3-Me-cyclopentyl | |
| 3.71 | —COCH₂OCH₃ | —CF₃ | —CH₃ | H | 4-Me-cyclohexyl | |
| 3.72 | —COCH₂OCH₃ | —CF₃ | —CH₃ | H | 3-Me-cyclohexyl | |
| 3.73 | —COCH₂OCH₃ | —CF₃ | —CH₃ | H | cycloheptyl | |
| 3.74 | —COCH₂OCH₃ | —CF₃ | —CH₃ | H | 2,4-dimethylpentan-3-yl | |
| 3.75 | —COCH₂OCH₃ | —CF₃ | —CH₃ | F | 4-Cl-phenyl | |
| 3.76 | —COCH₂OCH₂CH₃ | —CF₃ | —CH₃ | H | 4-F-phenyl | |
| 3.77 | —COCH₂OCH₂CH₃ | —CF₃ | —CH₃ | H | 4-Cl-phenyl | |
| 3.78 | —COCH₂OCH₂CH₃ | —CF₃ | —CH₃ | H | 4-Br-phenyl | |
| 3.79 | —COCH₂OCH₂CH₃ | —CF₃ | —CH₃ | H | 3-Me-cyclohexyl | |
| 3.80 | —COCH₂OCH₂CH₃ | —CF₃ | —CH₃ | H | cycloheptyl | |
| 3.81 | —COCH₂OCH₂CH₃ | —CF₃ | —CH₃ | H | 2,4-dimethylpentan-3-yl | |
| 3.82 | —COOCH₃ | —CF₃ | —CH₃ | H | 4-F-phenyl | |
| 3.83 | —COOCH₃ | —CF₃ | —CH₃ | H | 4-Cl-phenyl | |
| 3.84 | —COOCH₃ | —CF₃ | —CH₃ | H | 4-Br-phenyl | |
| 3.85 | —COOCH₃ | —CF₃ | —CH₃ | H | 3-Me-cyclopentyl | |
| 3.86 | —COOCH₃ | —CF₃ | —CH₃ | H | 4-Me-cyclohexyl | |

TABLE 3-continued

Pyrrolecarboxamides

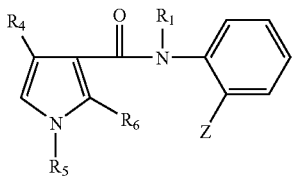

(Ib)

| Cmpd. no. | R$_1$ | R$_4$ | R$_5$ | R$_6$ | Z | phys. data m.p. ° C. |
|---|---|---|---|---|---|---|
| 3.87 | —COOCH$_3$ | —CF$_3$ | —CH$_3$ | H | 3-Me-cyclohexyl | |
| 3.88 | —COOCH$_3$ | —CF$_3$ | —CH$_3$ | H | cycloheptyl | |
| 3.89 | —COOCH$_3$ | —CF$_3$ | —CH$_3$ | H | ![2,4-dimethylpentyl] | |
| 3.90 | —COOCH$_3$ | —CF$_3$ | —CH$_3$ | F | 4-F-phenyl | |
| 3.91 | —COOCH$_3$ | —CF$_3$ | —CH$_3$ | F | 4-Cl-phenyl | |
| 3.92 | —COOCH$_3$ | —CF$_3$ | —CH$_3$ | F | cycloheptyl | |
| 3.93 | —CH=C=CH$_2$ | —CF$_3$ | —CH$_3$ | H | 4-F-phenyl | |
| 3.94 | —CH=C=CH$_2$ | —CF$_3$ | —CH$_3$ | H | 4-Cl-phenyl | |
| 3.95 | —CH=C=CH$_2$ | —CF$_3$ | —CH$_3$ | H | 4-Bromophenyl | 162-163 |

TABLE 4

Thiazolecarboxamides

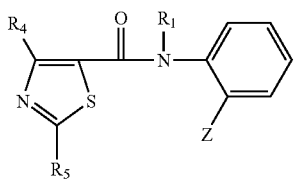

(Ic)

| Cmpd. no. | R$_1$ | R$_4$ | R$_5$ | Z | phys. data m.p. ° C. |
|---|---|---|---|---|---|
| 4.01 | —CH$_2$CH=CH$_2$ | —CF$_3$ | —CH$_3$ | 4-Cl-phenyl | |
| 4.02 | —CH$_2$CH=CH$_2$ | —CF$_3$ | —CH$_3$ | 4-Br-phenyl | |
| 4.03 | —CH$_2$CH=CH$_2$ | —CF$_3$ | —CH$_3$ | 4-Me-cyclohexyl | |
| 4.04 | —CH$_2$CH=CH$_2$ | —CF$_3$ | —CH$_3$ | 3-Me-cyclohexyl | |
| 4.05 | —CH$_2$CH=CH$_2$ | —CF$_3$ | —CH$_3$ | cycloheptyl | |
| 4.06 | —CH$_2$CH=CH$_2$ | —CF$_3$ | —CH$_3$ | ![2,4-dimethylpentyl] | |
| 4.07 | —CH$_2$C≡CH | —CF$_3$ | —CH$_3$ | 4-F-phenyl | |
| 4.08 | —CH$_2$C≡CH | —CF$_3$ | —CH$_3$ | 4-Cl-phenyl | |
| 4.09 | —CH$_2$C≡CH | —CF$_3$ | —CH$_3$ | 4-Br-phenyl | |
| 4.10 | —CH$_2$C≡CH | —CF$_3$ | —CH$_3$ | 3-Me-cyclopentyl | |
| 4.11 | —CH$_2$C≡CH | —CF$_3$ | —CH$_3$ | 4-Me-cyclohexyl | |
| 4.12 | —CH$_2$C≡CH | —CF$_3$ | —CH$_3$ | 3-Me-cyclohexyl | |
| 4.13 | —CH$_2$C≡CH | —CF$_3$ | —CH$_3$ | cycloheptyl | |
| 4.14 | —CH$_2$C≡CH | —CF$_3$ | —CH$_3$ | ![2,4-dimethylpentyl] | |
| 4.15 | —CH$_2$C≡CH | —CF$_3$ | —CH$_2$OCH$_3$ | 4-F-phenyl | |
| 4.16 | —CH$_2$C≡CH | —CF$_3$ | —CH$_2$OCH$_3$ | 4-Cl-phenyl | |
| 4.17 | —CH$_2$C≡CH | —CF$_3$ | —CH$_2$OCH$_3$ | cycloheptyl | |

TABLE 4-continued

Thiazolecarboxamides

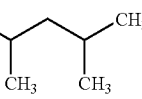

(Ic)

| Cmpd. no. | R$_1$ | R$_4$ | R$_5$ | Z | phys. data m.p. ° C. |
|---|---|---|---|---|---|
| 4.18 | —CH$_2$C≡CH | —CF$_3$ | —CH$_2$OCH$_3$ | 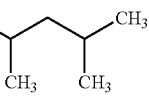 | |
| 4.19 | —COCH$_3$ | —CF$_3$ | —CH$_3$ | 4-Cl-phenyl | |
| 4.20 | —COCH$_3$ | —CF$_3$ | —CH$_3$ | 4-Br-phenyl | |
| 4.21 | —COCH$_3$ | —CF$_3$ | —CH$_3$ | 3-Me-cyclopentyl | |
| 4.22 | —COCH$_3$ | —CF$_3$ | —CH$_3$ | 4-Me-cyclohexyl | |
| 4.23 | —COCH$_3$ | —CF$_3$ | —CH$_3$ | 3-Me-cyclohexyl | |
| 4.24 | —COCH$_3$ | —CF$_3$ | —CH$_3$ | cycloheptyl | |
| 4.25 | —COCH$_3$ | —CF$_3$ | —CH$_3$ | 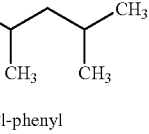 | |
| 4.26 | —COCH$_2$CH$_3$ | —CF$_3$ | —CH$_3$ | 4-F-phenyl | |
| 4.27 | —COCH$_2$CH$_3$ | —CF$_3$ | —CH$_3$ | 4-Cl-phenyl | |
| 4.28 | —COCH$_2$CH$_3$ | —CF$_3$ | —CH$_3$ | 4-Br-phenyl | |
| 4.29 | —COCH$_2$CH$_3$ | —CF$_3$ | —CH$_3$ | cycloheptyl | |
| 4.30 | —COCH$_2$CH$_3$ | —CF$_3$ | —CH$_3$ | 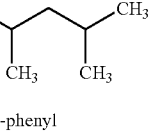 | |
| 4.31 | —COCH$_2$OCH$_3$ | —CF$_3$ | —CH$_3$ | 4-Cl-phenyl | |
| 4.32 | —COCH$_2$OCH$_3$ | —CF$_3$ | —CH$_3$ | 4-Br-phenyl | |
| 4.33 | —COCH$_2$OCH$_3$ | —CF$_3$ | —CH$_3$ | 3-Me-cyclopentyl | |
| 4.34 | —COCH$_2$OCH$_3$ | —CF$_3$ | —CH$_3$ | 4-Me-cyclohexyl | |
| 4.35 | —COCH$_2$OCH$_3$ | —CF$_3$ | —CH$_3$ | 3-Me-cyclohexyl | |
| 4.36 | —COCH$_2$OCH$_3$ | —CF$_3$ | —CH$_3$ | cycloheptyl | |
| 4.37 | —COCH$_2$OCH$_3$ | —CF$_3$ | —CH$_3$ | 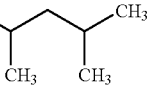 | |
| 4.38 | —COCH$_2$OCH$_2$CH$_3$ | —CF$_3$ | —CH$_3$ | 4-F-phenyl | |
| 4.39 | —COCH$_2$OCH$_2$CH$_3$ | —CF$_3$ | —CH$_3$ | 4-Cl-phenyl | |
| 4.40 | —COCH$_2$OCH$_2$CH$_3$ | —CF$_3$ | —CH$_3$ | cycloheptyl | |
| 4.41 | —COCH$_2$OCH$_2$CH$_3$ | —CF$_3$ | —CH$_3$ | 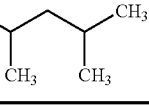 | |
| 4.42 | —COOCH$_3$ | —CF$_3$ | —CH$_3$ | 4-F-phenyl | resin |
| 4.43 | —COOCH$_3$ | —CF$_3$ | —CH$_3$ | 4-Cl-phenyl | |
| 4.44 | —COOCH$_3$ | —CF$_3$ | —CH$_3$ | 4-Br-phenyl | |
| 4.45 | —COOCH$_3$ | —CF$_3$ | —CH$_3$ | cycloheptyl | |
| 4.46 | —COOCH$_3$ | —CF$_3$ | —CH$_3$ |  | |

TABLE 5

Oxazolecarboxamides

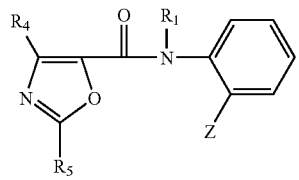

(Id)

| Cmpd. no. | $R_1$ | $R_4$ | $R_5$ | Z | phys. data m.p. ° C. |
|---|---|---|---|---|---|
| 5.01 | —CH$_2$CH=CH$_2$ | —CF$_3$ | —CH$_3$ | 4-Cl-phenyl | |
| 5.02 | —CH$_2$CH=CH$_2$ | —CF$_3$ | —CH$_3$ | 4-Br-phenyl | |
| 5.03 | —CH$_2$CH=CH$_2$ | —CF$_3$ | —CH$_3$ | 4-Me-cyclohexyl | |
| 5.04 | —CH$_2$CH=CH$_2$ | —CF$_3$ | —CH$_3$ | 3-Me-cyclohexyl | |
| 5.05 | —CH$_2$CH=CH$_2$ | —CF$_3$ | —CH$_3$ | cycloheptyl | |
| 5.06 | —CH$_2$CH=CH$_2$ | —CF$_3$ | —CH$_3$ | ![2,4-dimethylpentan-3-yl] | |
| 5.07 | —CH$_2$C≡CH | —CF$_3$ | —CH$_3$ | 4-F-phenyl | |
| 5.08 | —CH$_2$C≡CH | —CF$_3$ | —CH$_3$ | 4-Cl-phenyl | |
| 5.09 | —CH$_2$C≡CH | —CF$_3$ | —CH$_3$ | 4-Br-phenyl | |
| 5.10 | —CH$_2$C≡CH | —CF$_3$ | —CH$_3$ | 3-Me-cyclopentyl | |
| 5.11 | —CH$_2$C≡CH | —CF$_3$ | —CH$_3$ | 4-Me-cyclohexyl | |
| 5.12 | —CH$_2$C≡CH | —CF$_3$ | —CH$_3$ | 3-Me-cyclohexyl | |
| 5.13 | —CH$_2$C≡CH | —CF$_3$ | —CH$_3$ | cycloheptyl | |
| 5.14 | —CH$_2$C≡CH | —CF$_3$ | —CH$_3$ | ![2,4-dimethylpentan-3-yl] | |
| 5.15 | —CH$_2$C≡CH | —CF$_3$ | —CH$_2$OCH$_3$ | 4-F-phenyl | |
| 5.16 | —CH$_2$C≡CH | —CF$_3$ | —CH$_2$OCH$_3$ | 4-Cl-phenyl | |
| 5.17 | —CH$_2$C≡CH | —CF$_3$ | —CH$_2$OCH$_3$ | cycloheptyl | |
| 5.18 | —CH$_2$C≡CH | —CF$_3$ | —CH$_2$OCH$_3$ | ![2,4-dimethylpentan-3-yl] | |
| 5.19 | —COCH$_3$ | —CF$_3$ | —CH$_3$ | 4-Cl-phenyl | |
| 5.20 | —COCH$_3$ | —CF$_3$ | —CH$_3$ | 4-Br-phenyl | |
| 5.21 | —COCH$_3$ | —CF$_3$ | —CH$_3$ | 3-Me-cyclopentyl | |
| 5.22 | —COCH$_3$ | —CF$_3$ | —CH$_3$ | 4-Me-cyclohexyl | |
| 5.23 | —COCH$_3$ | —CF$_3$ | —CH$_3$ | 3-Me-cyclohexyl | |
| 5.24 | —COCH$_3$ | —CF$_3$ | —CH$_3$ | cycloheptyl | |
| 5.25 | —COCH$_3$ | —CF$_3$ | —CH$_3$ | ![2,4-dimethylpentan-3-yl] | |
| 5.26 | —COCH$_2$CH$_3$ | —CF$_3$ | —CH$_3$ | 4-F-phenyl | |
| 5.27 | —COCH$_2$CH$_3$ | —CF$_3$ | —CH$_3$ | 4-Cl-phenyl | |
| 5.28 | —COCH$_2$CH$_3$ | —CF$_3$ | —CH$_3$ | 4-Br-phenyl | |
| 5.29 | —COCH$_2$CH$_3$ | —CF$_3$ | —CH$_3$ | cycloheptyl | |
| 5.30 | —COCH$_2$CH$_3$ | —CF$_3$ | —CH$_3$ | ![2,4-dimethylpentan-3-yl] | |
| 5.31 | —COCH$_2$OCH$_3$ | —CF$_3$ | —CH$_3$ | 4-F-phenyl | |
| 5.32 | —COCH$_2$OCH$_3$ | —CF$_3$ | —CH$_3$ | 4-Cl-phenyl | |
| 5.33 | —COCH$_2$OCH$_3$ | —CF$_3$ | —CH$_3$ | 3-Me-cyclopentyl | |
| 5.34 | —COCH$_2$OCH$_3$ | —CF$_3$ | —CH$_3$ | 4-Me-cyclohexyl | |
| 5.35 | —COCH$_2$OCH$_3$ | —CF$_3$ | —CH$_3$ | 3-Me-cyclohexyl | |
| 5.36 | —COCH$_2$OCH$_3$ | —CF$_3$ | —CH$_3$ | cycloheptyl | |

TABLE 5-continued

Oxazolecarboxamides

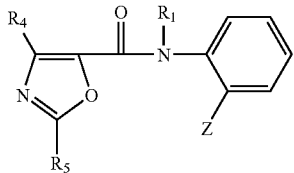

(Id)

| Cmpd. no. | R$_1$ | R$_4$ | R$_5$ | Z | phys. data m.p. ° C. |
|---|---|---|---|---|---|
| 5.37 | —COCH$_2$OCH$_3$ | —CF$_3$ | —CH$_3$ | (2,4-dimethylpentan-3-yl) | |
| 5.38 | —COCH$_2$OCH$_2$CH$_3$ | —CF$_3$ | —CH$_3$ | 4-F-phenyl | |
| 5.39 | —COCH$_2$OCH$_2$CH$_3$ | —CF$_3$ | —CH$_3$ | 4-Cl-phenyl | |
| 5.40 | —COCH$_2$OCH$_2$CH$_3$ | —CF$_3$ | —CH$_3$ | cycloheptyl | |
| 5.41 | —COCH$_2$OCH$_2$CH$_3$ | —CF$_3$ | —CH$_3$ | (2,4-dimethylpentan-3-yl) | |
| 5.42 | —COOCH$_3$ | —CF$_3$ | —CH$_3$ | 4-F-phenyl | |
| 5.43 | —COOCH$_3$ | —CF$_3$ | —CH$_3$ | 4-Cl-phenyl | |
| 5.44 | —COOCH$_3$ | —CF$_3$ | —CH$_3$ | 4-Br-phenyl | |
| 5.45 | —COOCH$_3$ | —CF$_3$ | —CH$_3$ | cycloheptyl | |
| 5.46 | —COOCH$_3$ | —CF$_3$ | —CH$_3$ | (2,4-dimethylpentan-3-yl) | |

TABLE 6

Pyridine carboxylic acid amides

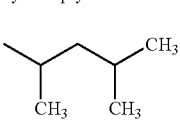

(Ie)

| Cmpd. no. | R$_1$ | R$_4$ | Z | phys. data m.p. ° C. |
|---|---|---|---|---|
| 6.01 | —CH$_2$CH=CH$_2$ | —Cl | 4-F-phenyl | |
| 6.02 | —CH$_2$CH=CH$_2$ | —Cl | 4-Cl-phenyl | |
| 6.03 | —CH$_2$CH=CH$_2$ | —Cl | 4-Br-phenyl | |
| 6.04 | —CH$_2$CH=CH$_2$ | —Cl | cycloheptyl | |
| 6.05 | —CH$_2$CH=CH$_2$ | —Cl | (2,4-dimethylpentan-3-yl) | |
| 6.06 | —CH$_2$C≡CH | —CF$_3$ | 4-F-phenyl | |
| 6.07 | —CH$_2$C≡CH | —CF$_3$ | 4-Cl-phenyl | |
| 6.08 | —CH$_2$C≡CH | —CF$_3$ | 4-Br-phenyl | |
| 6.09 | —CH$_2$C≡CH | —CF$_3$ | cycloheptyl | |
| 6.10 | —CH$_2$C≡CH | —CF$_3$ | (2,4-dimethylpentan-3-yl) | |
| 6.11 | —CH$_2$C≡CH | —Cl | 4-F-phenyl | |
| 6.12 | —CH$_2$C≡CH | —Cl | 4-Cl-phenyl | |
| 6.13 | —CH$_2$C≡CH | —Cl | 4-Br-phenyl | |
| 6.14 | —CH$_2$C≡CH | —Cl | cycloheptyl | |
| 6.15 | —CH$_2$C≡CH | —Cl | (2,4-dimethylpentan-3-yl) | |
| 6.16 | —CH$_2$C≡CH | —CF$_3$ | 4-F-phenyl | |
| 6.17 | —CH$_2$C≡CH | —CF$_3$ | 4-Cl-phenyl | |

TABLE 6-continued

Pyridine carboxylic acid amides

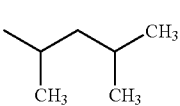
(Ie)

| Cmpd. no. | R₁ | R₄ | Z | phys. data m.p. ° C. |
|---|---|---|---|---|
| 6.18 | —CH₂C≡CH | —CF₃ | 4-Br-phenyl | |
| 6.19 | —CH₂C≡CH | —CF₃ | cycloheptyl | |
| 6.20 | —CH₂C≡CH | —CF₃ | 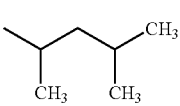 | |
| 6.21 | —COCH₃ | —Cl | 4-F-phenyl | |
| 6.22 | —COCH₃ | —Cl | 4-Cl-phenyl | |
| 6.23 | —COCH₃ | —Cl | 4-Br-phenyl | |
| 6.24 | —COCH₃ | —Cl | 4-Me-cyclohexyl | |
| 6.25 | —COCH₃ | —Cl | 3-Me-cyclohexyl | |
| 6.26 | —COCH₃ | —Cl | cycloheptyl | |
| 6.27 | —COCH₃ | —Cl | 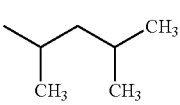 | |
| 6.28 | —COCH₃ | —CF₃ | 4-F-phenyl | |
| 6.29 | —COCH₃ | —CF₃ | 4-Cl-phenyl | |
| 6.30 | —COCH₃ | —CF₃ | 4-Br-phenyl | |
| 6.31 | —COCH₃ | —CF₃ | 4-Me-cyclohexyl | |
| 6.32 | —COCH₃ | —CF₃ | 3-Me-cyclohexyl | |
| 6.33 | —COCH₃ | —CF₃ | cycloheptyl | |
| 6.34 | —COCH₃ | —CF₃ | 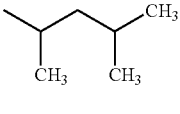 | |
| 6.35 | —COCH₂CH₃ | —Cl | 4-F-phenyl | |
| 6.36 | —COCH₂CH₃ | —Cl | 4-Cl-phenyl | |
| 6.37 | —COCH₂CH₃ | —Cl | 4-Br-phenyl | |
| 6.38 | —COCH₂CH₃ | —Cl | 3-Me-cyclohexyl | |
| 6.39 | —COCH₂CH₃ | —Cl | cycloheptyl | |
| 6.40 | —COCH₂CH₃ | —Cl | 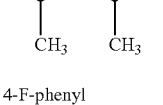 | |
| 6.41 | —COCH₂CH₃ | —CF₃ | 4-F-phenyl | |
| 6.42 | —COCH₂CH₃ | —CF₃ | 4-Cl-phenyl | |
| 6.43 | —COCH₂CH₃ | —CF₃ | 4-Br-phenyl | |
| 6.44 | —COCH₂CH₃ | —CF₃ | cycloheptyl | |
| 6.45 | —COCH₂CH₃ | —CF₃ | 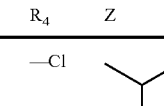 | |
| 6.46 | —COCH₂OCH₃ | —Cl | 4-F-phenyl | |
| 6.47 | —COCH₂OCH₃ | —Cl | 4-Cl-phenyl | |
| 6.48 | —COCH₂OCH₃ | —Cl | 4-Br-phenyl | |
| 6.49 | —COCH₂OCH₃ | —Cl | cycloheptyl | |
| 6.50 | —COCH₂OCH₃ | —Cl | 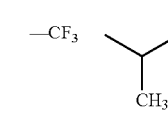 | |
| 6.51 | —COCH₂OCH₃ | —CF₃ | 4-F-phenyl | |
| 6.52 | —COCH₂OCH₃ | —CF₃ | 4-Cl-phenyl | |
| 6.53 | —COCH₂OCH₃ | —CF₃ | 4-Br-phenyl | |
| 6.54 | —COCH₂OCH₃ | —CF₃ | cycloheptyl | |
| 6.55 | —COCH₂OCH₃ | —CF₃ | 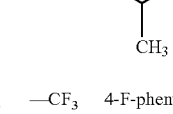 | |
| 6.56 | —COCH₂OCH₂CH₃ | —Cl | 4-F-phenyl | |
| 6.57 | —COCH₂OCH₂CH₃ | —Cl | 4-Cl-phenyl | |
| 6.58 | —COCH₂OCH₂CH₃ | —Cl | cycloheptyl | |
| 6.59 | —COCH₂OCH₂CH₃ | —Cl | 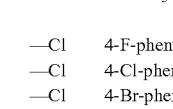 | |
| 6.60 | —COCH₂OCH₂CH₃ | —CF₃ | 4-F-phenyl | |
| 6.61 | —COCH₂OCH₂CH₃ | —CF₃ | 4-Cl-phenyl | |
| 6.62 | —COCH₂OCH₂CH₃ | —CF₃ | cycloheptyl | |
| 6.63 | —COCH₂OCH₂CH₃ | —CF₃ | 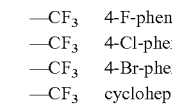 | |
| 6.64 | —COOCH₃ | —Cl | 4-F-phenyl | |
| 6.65 | —COOCH₃ | —Cl | 4-Cl-phenyl | |
| 6.66 | —COOCH₃ | —Cl | 4-Br-phenyl | |
| 6.67 | —COOCH₃ | —Cl | cycloheptyl | |
| 6.68 | —COOCH₃ | —Cl | 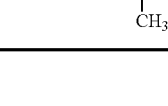 | |
| 6.69 | —COOCH₃ | —CF₃ | 4-F-phenyl | |
| 6.70 | —COOCH₃ | —CF₃ | 4-Cl-phenyl | |
| 6.71 | —COOCH₃ | —CF₃ | 4-Br-phenyl | |
| 6.72 | —COOCH₃ | —CF₃ | cycloheptyl | |
| 6.73 | —COOCH₃ | —CF₃ | (CH₃)₂CH-CH₂-CH(CH₃)- | |

TABLE 7

Compounds of the general formula If

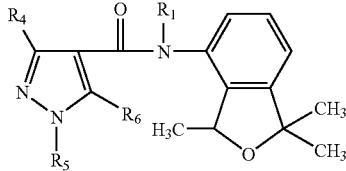

(If)

| Cmpd. no. | $R_1$ | $R_4$ | $R_5$ | $R_6$ | phys. data m.p. °C. |
|---|---|---|---|---|---|
| 7.01 | —CH$_2$CH=CH$_2$ | —CF$_3$ | —CH$_3$ | H | |
| 7.02 | —CH$_2$CH=CH$_2$ | —CF$_3$ | —CH$_3$ | F | |
| 7.03 | —CH$_2$CH=CH$_2$ | —CF$_2$H | —CH$_3$ | H | |
| 7.04 | —CH$_2$C≡CH | —CF$_3$ | —CH$_3$ | H | |
| 7.05 | —CH$_2$C≡CH | —CF$_3$ | —CH$_3$ | F | |
| 7.06 | —CH$_2$C≡CH | —CF$_2$H | —CH$_3$ | H | |
| 7.07 | —COCH$_3$ | —CF$_3$ | —CH$_3$ | H | |
| 7.08 | —COCH$_3$ | —CF$_2$H | —CH$_3$ | H | |
| 7.09 | —COCH$_2$CH$_3$ | —CF$_3$ | —CH$_3$ | H | |
| 7.10 | —COCH$_2$CH$_3$ | —CF$_2$H | —CH$_3$ | H | |
| 7.11 | —COCH$_2$OCH$_3$ | —CF$_3$ | —CH$_3$ | H | |
| 7.12 | —COCH$_2$OCH$_3$ | —CF$_2$H | —CH$_3$ | H | |
| 7.13 | —COCH$_2$OCH$_3$ | —CF$_3$ | —CH$_3$ | F | |
| 7.14 | —COCH$_2$OCH$_2$CH$_3$ | —CF$_3$ | —CH$_3$ | H | |
| 7.15 | —COCH$_2$OCH$_2$CH$_3$ | —CF$_2$H | —CH$_3$ | H | |
| 7.16 | —COCH$_2$OCH$_2$CH$_3$ | —CF$_3$ | —CH$_3$ | F | |
| 7.17 | —COOCH$_3$ | —CF$_3$ | —CH$_3$ | H | |
| 7.18 | —COOCH$_3$ | —CF$_2$H | —CH$_3$ | H | |
| 7.19 | —COOCH$_3$ | —CF$_3$ | —CH$_3$ | F | |
| 7.20 | —COOCH$_3$ | —CF$_2$H | —CH$_3$ | F | |

TABLE 8

Compounds of the general formula Ig

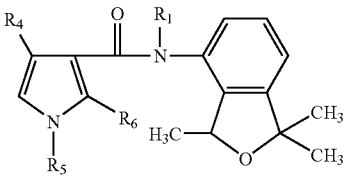

(Ig)

| Cmpd. no. | $R_1$ | $R_4$ | $R_5$ | $R_6$ | phys. data m.p. °C. |
|---|---|---|---|---|---|
| 8.01 | —CH$_2$CH=CH$_2$ | —CF$_3$ | —CH$_3$ | H | |
| 8.02 | —CH$_2$CH=CH$_2$ | —CF$_3$ | —CH$_2$OCH$_3$ | H | |
| 8.03 | —CH$_2$C≡CH | —CF$_3$ | —CH$_3$ | H | resin |
| 8.04 | —CH$_2$C≡CH | —CF$_3$ | —CH$_2$OCH$_3$ | H | |
| 8.05 | —CH$_2$C≡CH | —CF$_3$ | —CH$_3$ | F | |
| 8.06 | —COCH$_3$ | —CF$_3$ | —CH$_3$ | H | |
| 8.07 | —COCH$_3$ | —CF$_3$ | —CH$_2$OCH$_3$ | H | |
| 8.08 | —COCH$_2$CH$_3$ | —CF$_3$ | —CH$_3$ | H | |
| 8.09 | —COCH$_2$CH$_3$ | —CF$_3$ | —CH$_2$OCH$_3$ | H | |
| 8.10 | —COCH$_2$OCH$_3$ | —CF$_3$ | —CH$_3$ | H | |
| 8.11 | —COCH$_2$OCH$_3$ | —CF$_3$ | —CH$_3$ | F | |
| 8.12 | —COCH$_2$OCH$_3$ | —CF$_3$ | —CH$_2$OCH$_3$ | H | |
| 8.13 | —COCH$_2$OCH$_2$CH$_3$ | —CF$_3$ | —CH$_3$ | H | |
| 8.14 | —COCH$_2$OCH$_2$CH$_3$ | —CF$_3$ | —CH$_2$OCH$_3$ | H | |
| 8.15 | —COOCH$_3$ | —CF$_3$ | —CH$_3$ | H | |
| 8.16 | —COOCH$_3$ | —CF$_3$ | —CH$_2$OCH$_3$ | H | |
| 8.17 | —COOCH$_3$ | —CF$_3$ | —CH$_3$ | F | |

TABLE 9

Compounds of the general formula Ih

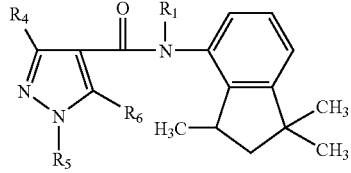

(Ih)

| Cmpd. no. | $R_1$ | $R_4$ | $R_5$ | $R_6$ | phys. data m.p. °C. |
|---|---|---|---|---|---|
| 9.01 | —CH$_2$CH=CH$_2$ | —CF$_3$ | —CH$_3$ | H | |
| 9.02 | —CH$_2$CH=CH$_2$ | —CF$_3$ | —CH$_3$ | F | |
| 9.03 | —CH$_2$CH=CH$_2$ | —CF$_2$H | —CH$_3$ | H | |
| 9.04 | —CH$_2$C≡CH | —CF$_3$ | —CH$_3$ | H | resin |
| 9.05 | —CH$_2$C≡CH | —CF$_3$ | —CH$_3$ | F | |
| 9.06 | —CH$_2$C≡CH | —CF$_2$H | —CH$_3$ | H | |
| 9.07 | —COCH$_3$ | —CF$_3$ | —CH$_3$ | H | |
| 9.08 | —COCH$_3$ | —CF$_2$H | —CH$_3$ | H | |
| 9.09 | —COCH$_2$CH$_3$ | —CF$_3$ | —CH$_3$ | H | |
| 9.10 | —COCH$_2$CH$_3$ | —CF$_2$H | —CH$_3$ | H | |
| 9.11 | —COCH$_2$OCH$_3$ | —CF$_3$ | —CH$_3$ | H | |
| 9.12 | —COCH$_2$OCH$_3$ | —CF$_2$H | —CH$_3$ | H | |
| 9.13 | —COCH$_2$OCH$_3$ | —CF$_3$ | —CH$_3$ | F | |
| 9.14 | —COCH$_2$OCH$_2$CH$_3$ | —CF$_3$ | —CH$_3$ | H | |
| 9.15 | —COCH$_2$OCH$_2$CH$_3$ | —CF$_2$H | —CH$_3$ | H | |
| 9.18 | —COOCH$_3$ | —CF$_2$H | —CH$_3$ | H | |
| 9.19 | —COOCH$_3$ | —CF$_3$ | —CH$_3$ | F | |
| 9.20 | —COOCH$_3$ | —CF$_2$H | —CH$_3$ | F | |

TABLE 10

Compounds of the general formula Ii

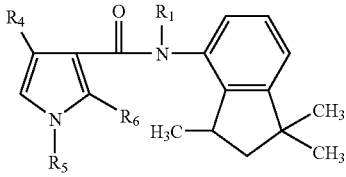

(Ii)

| Cmpd. no. | $R_1$ | $R_4$ | $R_5$ | $R_6$ | phys. data m.p. °C. |
|---|---|---|---|---|---|
| 10.01 | —CH$_2$CH=CH$_2$ | —CF$_3$ | —CH$_3$ | H | |
| 10.02 | —CH$_2$CH=CH$_2$ | —CF$_3$ | —CH$_2$OCH$_3$ | H | |
| 10.03 | —CH$_2$C≡CH | —CF$_3$ | —CH$_3$ | H | 142-144 |
| 10.04 | —CH$_2$C≡CH | —CF$_3$ | —CH$_2$OCH$_3$ | H | |
| 10.05 | —CH$_2$C≡CH | —CF$_3$ | —CH$_3$ | F | |
| 10.06 | —COCH$_3$ | —CF$_3$ | —CH$_3$ | H | |
| 10.07 | —COCH$_3$ | —CF$_3$ | —CH$_2$OCH$_3$ | H | |
| 10.08 | —COCH$_2$CH$_3$ | —CF$_3$ | —CH$_3$ | H | |
| 10.09 | —COCH$_2$CH$_3$ | —CF$_3$ | —CH$_2$OCH$_3$ | H | |
| 10.10 | —COCH$_2$OCH$_3$ | —CF$_3$ | —CH$_3$ | H | oil; $M^+ = 422$ |
| 10.11 | —COCH$_2$OCH$_3$ | —CF$_3$ | —CH$_3$ | F | |
| 10.12 | —COCH$_2$OCH$_3$ | —CF$_3$ | —CH$_2$OCH$_3$ | H | |
| 10.13 | —COCH$_2$OCH$_2$CH$_3$ | —CF$_3$ | —CH$_3$ | H | |
| 10.14 | —COCH$_2$OCH$_2$CH$_3$ | —CF$_3$ | —CH$_2$OCH$_3$ | H | |
| 10.15 | —COOCH$_3$ | —CF$_3$ | —CH$_3$ | H | |
| 10.16 | —COOCH$_3$ | —CF$_3$ | —CH$_2$OCH$_3$ | H | |
| 10.17 | —COOCH$_3$ | —CF$_3$ | —CH$_3$ | F | |

FORMULATION EXAMPLES FOR COMPOUNDS OF FORMULA I

Working procedures for preparing formulations of the compounds of formula I such as Emulsifiable concentrates, Solutions, Granulates, Dusts and Wettable powders are described in WO 97/33890.

BIOLOGICAL EXAMPLES

Fungicidal Actions

Example B-1

Action Against *Puccinia recondita* /Wheat (Brownrust on Wheat)

1 week old wheat plants cv. Arina are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation.

Compounds of Tables 1 to 10 show good activity in these tests. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-2

Action Against *Podosphaera leucotricha* /Apple (Powdery Mildew on Apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r. h. under a light regime of 14/10 h (light/dark) the disease incidence is assessed.

Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-3

Action Against *Venturia inaegualis* /Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r. h. the plants are placed for 4 days at 21° C. and 60% r. h. in a greenhouse. After another 4 day incubation period at 21° C. and 95% r. h. the disease incidence is assessed.

Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-4

Action Against *Erysiphe graminis* /Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r. h. in a greenhouse the disease incidence is assessed.

Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-5

Action Against *Botrytis cinerea* /Apple (Botrytis on Apple Fruits)

In an apple fruit cv. Golden Delicious 3 holes are drilled and each filled with 30 µl droplets of the formulated test compound (0.002% active ingredient). Two hours after application 50 µl of a spore suspension of *B. cinerea* ($4 \times 10^5$ conidia/ml) are pipetted on the application sites. After an incubation period of 7 days at 22° C. in a growth chamber the disease incidence is assessed.

Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-6

Action Against *Botrytis cinerea* /Grape (Botrytis on Grapes)

5 week old grape seedlings cv. Gutedel are treated with the formulated test compound (0.002% active ingredient) in a spray chamber. Two days after application grape plants are inoculated by spraying a spore suspension ($1 \times 10^6$ conidia/ml) on the test plants. After an incubation period of 4 days at 21° C. and 95% r. h. in a greenhouse the disease incidence is assessed.

Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-7

Action Against *Botrytis cinerea* /Tomato (Botryis on Tomatoes)

4 week old tomato plants cv. Roter Gnom are treated with the formulated test compound (0.002% active ingredient) in a spray chamber. Two days after application tomato plants are inoculated by spraying a spore suspension ($1 \times 10^5$ conidia/ml) on the test plants. After an incubation period of 4 days at 20° C. and 95% r. h. in a growth chamber the disease incidence is assessed.

Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-8

Action Against *Pyrenophora teres* /Barley (Net Blotch on Barley)

1 week old barley plants cv. Express are treated with the formulated test compound (0.002% active ingredient) in a spray chamber. Two days after application barley plants are inoculated by spraying a spore suspension ($3 \times 10^4$ conidia/ml) on the test plants. After an incubation period of 2 days at 20° C. and 95% r. h. plants are kept for 2 days at 20° C. and 60% r. h. in a greenhouse. The disease incidence is assessed 4 days after inoculation. Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

Example B-9

Action Against *Septoria nodorum* /Wheat (Septoria Leaf Spot on Wheat)

1 week old wheat plants cv. Arina are treated with the formulated test compound (0.02% active ingredient) in a spray chamber. One day after application wheat plants are inoculated by spraying a spore suspension ($5 \times 10^5$ conidia/ml) on the test plants. After an incubation period of 1 day at 20° C. and 95% r. h. plants are kept for 10 days at 20° C. and 60% r.h. in a greenhouse. The disease incidence is assessed 11 days after inoculation.

Compounds of Tables 1 to 10 show good activity in this test. The compounds 1.24, 1.50, 2.1, 2.7, 2.9, 2.15, 2.42, 2.56, 2.62, 2.68, 2.75, 2.85, 2.91, 3.1, 3.8, 3.28, 3.67, 3.74, 10.3 and 10.10 exhibit strong efficacy (<20% infestation).

What is claimed is:

1. A carboxamide of the formula I

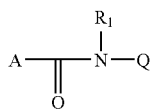

wherein

A is 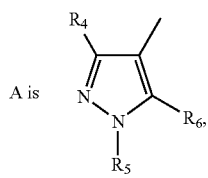 (A1)

Q is: 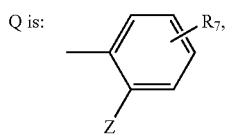 (Q1)

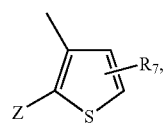 (Q2)

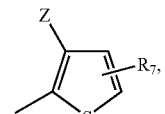 (Q3)

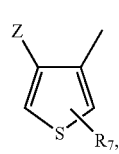 (Q4)

-continued

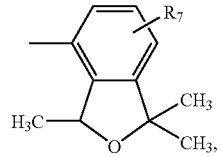 (Q5)

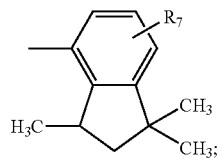 (Q6)

$R_1$ is

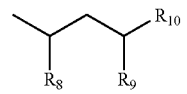

$CH_2CH=CHR_2$, $CH=C=CHR_2$ or $COR_3$;

$R_2$ is hydrogen, $C_1$-$C_6$alkyl, $C_1$-$C_6$haloalkyl, $C_2$-$C_6$alkenyl, $C_2$-$C_6$alkynyl, $C_3$-$C_7$cycloalkyl, $COOC_1$-$C_4$alkyl, $COOC_3$-$C_6$alkenyl, $COOC_3$-$C_6$alkynyl or CN;

$R_3$ is $C_1$-$C_6$alkyl, $C_1$-$C_6$alkyl substituted by halogen, $C_1$-$C_6$alkoxy or $C_1$-$C_6$haloalkoxy; or is $C_1$-$C_6$alkylthio, $C_1$-$C_6$haloalkylthio, $C_1$-$C_6$alkoxy, $C_1$-$C_6$haloalkoxy; $C_3$-$C_6$alkenyloxy or $C_3$-$C_6$haloalkenyloxy; $C_3$-$C_6$alkynyloxy or $C_3$-$C_6$haloalkynyloxy;

$R_4$ is methyl, $CF_2Cl$, $CF_3$, $CF_2H$, $CFH_2$, Cl or Br;

$R_5$ is methyl, $CF_3$, $CH_2OCH_3$ or $CH_2OCF_3$;

$R_6$ is hydrogen, fluoro, $CF_3$ or methyl;

$R_7$ is hydrogen, methyl or halogen; and

Z is phenyl, halophenyl, $C_5$-$C_7$cycloalkyl, $C_5$-$C_7$cycloalkyl substituted by $C_1$-$C_3$alkyl, $C_1$-$C_3$haloalkyl or halogen, or a group of the form $$\begin{array}{c} R_{10} \\ \diagup \\ R_8 \quad R_9 \end{array}$$

wherein $R_8$, $R_9$ and $R_{10}$ are independently of each other $C_1$-$C_3$alkyl.

2. A compound of formula I according to claim 1, wherein $R_2$ is hydrogen, $C_1$-$C_4$alkyl, $C_1$-$C_4$haloalkyl, $C_2$-$C_4$alkenyl, $C_2$-$C_4$alkynyl, $C_3$-$C_6$cycloalkyl, $COOC_1$-$C_4$alkyl, $COOC_3$-$C_4$alkenyl or $COOC_3$-$C_4$alkynyl;

$R_3$ is $C_1$-$C_6$alkyl, $C_1$-$C_6$alkyl substituted by fluoro, chloro, bromo, $C_1$-$C_6$alkoxy or $C_1$-$C_6$haloalkoxy; or is $C_1$-$C_4$alkoxy, $C_1$-$C_4$haloalkoxy; $C_3$-$C_4$alkenyloxy or $C_3$-$C_6$haloalkynyloxy.

3. A compound of formula I according to claim 2, wherein Q is Q1.

4. A compound of formula I according to claim 3, wherein Z is phenyl, halophenyl or a group of the form

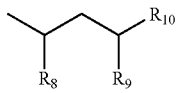

wherein $R_8$, $R_9$ and $R_{10}$ are independently of each other $C_1$-$C_3$alkyl.

5. A compound of formula I according to claim 3, wherein Z is $C_5$-$C_7$cycloalkyl unsubstituted or substituted by $C_1$-$C_3$alkyl, $C_1$-$C_3$haloalkyl or halogen.

6. A compound of formula I according to claim 2, wherein Q is Q5 or Q6.

7. A compound of formula I according to claim 2, wherein Q is Q2, Q3 or Q4.

8. A compound of formula according to claim 2, wherein Q is Q1 or Q6; and Z is phenyl, halophenyl or $C_5$-$C_7$cycloalkyl unsubstituted or substituted by $C_1$-$C_3$alkyl, $C_1$-$C_3$haloalkyl or halogen.

9. A compound according to claim 1, selected from the group consisting 1-methyl-4-trifluoromethyl-pyrazole-3-carboxylic acid (2-methoxyacetyl)-[2'(4-fluorophenyl)phenyl]amide, 1-methyl-4-trifluoromethyl-pyrazole-3-carboxylic acid (2-methoxyacetyl)-[2'(4-chlorophenyl)phenyl]amide, 1-methyl-4-trifluoromethyl-pyrazole-3-carboxylic acid (2-propargyl)-[2'(4-fluorophenyl)phenyl]amide, 1-methyl-4-trifluoromethyl-pyrazole-3-carboxylic acid (2-propargyl)-[2'(4-chlorophenyl)phenyl]amide, 1-methyl-4-trifluoromethyl-pyrazole-3-carboxylic acid (2-acetyl)-[2'(4-fluorophenyl)phenyl]amide, 1-methyl-4-trifluoromethyl-pyrazole-3-carboxylic acid (2-acetyl)-[2'(4-chlorophenyl)phenyl]amide, 1-methoxymethyl-4-trifluoromethyl-pyrazole-3-carboxylic acid (2-methoxyacetyl)-[2'(4-fluorophenyl)phenyl]amide, 1-methoxymethyl-4-trifluoromethyl-pyrazole-3-carboxylic acid (2-methoxyacetyl)-[2'(4-chlorophenyl)phenyl]amide, 1-methoxymethyl-4-trifluoromethyl-pyrazole-3-carboxylic acid (2-propargyl)-[2'(4-fluorophenyl)phenyl]amide, 1-methoxymethyl-4-trifluoromethyl-pyrazole-3-carboxylic acid (2-propargyl)-[2'(4-chlorophenyl)phenyl]amide, 1-methoxymethyl-4-trifluoromethyl-pyrazole-3-carboxylic acid (2-acetyl)-[2'(4-fluorophenyl)phenyl]amide, 1-methoxymethyl-4-trifluoromethyl-pyrazole-3-carboxylic acid (2-acetyl)-[2'(4-chlorophenyl)phenyl]amide, 1-methyl-4-difluoromethyl-pyrazole-3-carboxylic acid (2-methoxyacetyl)-[2'(4-fluorophenyl)phenyl]amide, 1-methyl-4-difluoromethyl-pyrazole-3-carboxylic acid (2-methoxyacetyl)-[2'(4-chlorophenyl)phenyl]amide, 1-methyl-4-difluoromethyl-pyrazole-3-carboxylic acid (2-propargyl)-[2'(4-fluorophenyl)phenyl]amide, 1-methyl-4-difluoromethyl-pyrazole-3-carboxylic acid (2-propargyl)-[2'(4-chlorophenyl)phenyl]amide, 1-methyl-4-difluoromethyl-pyrazole-3-carboxylic acid (2-acetyl)-[2'(4-fluorophenyl)phenyl]amide, 1-methyl-4-difluoromethyl-pyrazole-3-carboxylic acid (2-acetyl)-[2'(4-chlorophenyl)phenyl]amide, 1-methoxymethyl-4-difluoromethyl-pyrazole-3-carboxylic acid (2-methoxyacetyl)-[2'(4-fluorophenyl)phenyl]amide, 1-methoxymethyl-4-difluoromethyl-pyrazole-3-carboxylic acid (2-methoxyacetyl)-[2'(4-chlorophenyl)phenyl]amide, 1-methoxymethyl-4-difluoromethyl-pyrazole-3-carboxylic acid (2-propargyl)-[2'(4-fluorophenyl)phenyl]amide, 1-methoxymethyl-4-difluoromethyl-pyrazole-3-carboxylic acid (2-propargyl)-[2'(4-chlorophenyl)phenyl]amide, 1-methoxymethyl-4-difluoromethyl-pyrazole-3-carboxylic acid (2-acetyl)-[2'(4-fluorophenyl)phenyl]amide, and 1-methoxymethyl-4-difluoromethyl-pyrazole-3-carboxylic acid (2-acetyl)-[2'(4-chlorophenyl)phenyl]amide.

10. A fungicidal composition comprising the compound as claimed in claim 1, together with a suitable carrier, capable of for controlling a microorganism selected from the group consisting of *Puccinia recondita, Podosphaera leucotricha, Venturia inaequalis, Erysiphe graminis, Botrytis cinerea, Pyrenophora teres* and *Septoria nodorum*.

11. A method of controlling infestation of cultivated plants by microorganisms selected from the group consisting of *Puccinia recondite, Podosphaera leucotricha, Venturia inaequalis, Erysiphe graminis, Botrytis cinerea, Pyrenophora teres* and *Septoria nodorum*, comprising application to the plants, parts thereof or the locus thereof of a composition comprising the compound as claimed in claim 1.

* * * * *

UNITED STATES PATENT AND TRADEMARK OFFICE
CERTIFICATE OF CORRECTION

PATENT NO. : 7,332,518 B2  Page 1 of 1
APPLICATION NO. : 10/470069
DATED : February 19, 2008
INVENTOR(S) : Harald Walter and Stephan Trah It is certified that error appears in the above-identified patent and that said Letters Patent is hereby corrected as shown below:

IN THE CLAIMS:

In Claim 10, line 3, delete "capable of".

Signed and Sealed this
Twenty-first Day of June, 2011

David J. Kappos
*Director of the United States Patent and Trademark Office*

UNITED STATES PATENT AND TRADEMARK OFFICE
CERTIFICATE OF CORRECTION

PATENT NO. : 7,332,518 B2  
APPLICATION NO. : 10/470069  
DATED : February 19, 2008  
INVENTOR(S) : Harald Walter and Stephan Trah Page 1 of 1

It is certified that error appears in the above-identified patent and that said Letters Patent is hereby corrected as shown below:

IN THE CLAIMS:

Column 48, line 36 (Claim 10, line 3) delete "capable of".

This certificate supersedes the Certificate of Correction issued June 21, 2011.

Signed and Sealed this
Twenty-sixth Day of July, 2011

David J. Kappos
*Director of the United States Patent and Trademark Office*